(12) United States Patent
Erjefält

(10) Patent No.: US 9,311,521 B2
(45) Date of Patent: Apr. 12, 2016

(54) METHOD FOR PROVIDING IMAGES OF A TISSUE SECTION

(75) Inventor: Jonas Erjefält, Södra Sandby (SE)

(73) Assignee: MEDETECT AB, Lund (SE)

( * ) Notice: Subject to any disclaimer, the term of this patent is extended or adjusted under 35 U.S.C. 154(b) by 113 days.

(21) Appl. No.: 14/233,002

(22) PCT Filed: Jul. 27, 2012

(86) PCT No.: PCT/SE2012/050851
§ 371 (c)(1),
(2), (4) Date: Jan. 28, 2014

(87) PCT Pub. No.: WO2013/015740
PCT Pub. Date: Jan. 31, 2013

(65) Prior Publication Data
US 2014/0140607 A1 May 22, 2014

Related U.S. Application Data

(60) Provisional application No. 61/512,617, filed on Jul. 28, 2011.

(30) Foreign Application Priority Data

Jul. 28, 2011 (SE) ...................................... 1150724

(51) Int. Cl.
*G06K 9/00* (2006.01)
*G06T 7/00* (2006.01)
(Continued)

(52) U.S. Cl.
CPC ........ *G06K 9/00147* (2013.01); *G01N 33/5005* (2013.01); *G06K 9/0014* (2013.01); *G06T 7/0012* (2013.01); *G01N 1/30* (2013.01)

(58) Field of Classification Search
None
See application file for complete search history.

(56) References Cited

U.S. PATENT DOCUMENTS 7,194,118 B1 * 3/2007 Harris et al. .................. 382/128
8,116,551 B2    2/2012 Gallagher et al.
(Continued)

FOREIGN PATENT DOCUMENTS

WO    WO-2007129308 A2    11/2007
WO    WO-2009072098 A1    6/2009
WO    WO-2010115089 A2    10/2010

OTHER PUBLICATIONS

Extended European Search Report dated Apr. 7, 2015 issued in corresponding European Application No. 12818014.8.
(Continued)

*Primary Examiner* — Jon Chang
(74) *Attorney, Agent, or Firm* — Harness, Dickey & Pierce, P.L.C.

(57) ABSTRACT

A method for differentiating areas in a series of digital images, the method comprising the steps of: providing a series of images comprising undetermined marker areas; evaluating every image $1_n$ for $1 \le n \le N$ according to predetermined selection criteria and defining image marker areas as undetermined marker areas fulfilling the predetermined selection criteria; providing a new image $1_{new}$; and inserting new image marker areas in the new image $1_{new}$, said new image marker areas having the same shape and location as image marker areas present in image $1_n$ but not in image $1_{n-1}$, and said new image marker areas being identifiable in $1_{new}$ by a unique feature. Further, the application discloses a method for visualizing cell populations in tissue sections of a histological sample. Further, the application discloses a method for visualizing three-dimensional distribution of multiple cell populations in a histological sample.

20 Claims, 8 Drawing Sheets

(51) Int. Cl.
  *G01N 33/50*  (2006.01)
  *G01N 1/30*  (2006.01)

(56) References Cited

U.S. PATENT DOCUMENTS

| | | |
|---|---|---|
| 2008/0032321 A1 | 2/2008 | Ginty et al. |
| 2008/0032328 A1 | 2/2008 | Cline et al. |
| 2008/0166036 A1* | 7/2008 | Bloom et al. ............... 382/133 |
| 2009/0171203 A1 | 7/2009 | Avital et al. |
| 2009/0245610 A1 | 10/2009 | Can et al. |
| 2009/0318804 A1 | 12/2009 | Avital et al. |
| 2010/0164950 A1 | 7/2010 | Zhao et al. |
| 2010/0254589 A1 | 10/2010 | Gallagher |
| 2011/0091081 A1 | 4/2011 | Sarachan et al. |
| 2011/0122138 A1 | 5/2011 | Schmidt et al. |

OTHER PUBLICATIONS

Schubert, W. et al. "Analyzing proteome topology and function by automated multidimensional fluorescence microscopy." *Nature Biotechnology* (2006): 1-9.

* cited by examiner

METHOD FOR PROVIDING IMAGES OF A TISSUE SECTION

CROSS-REFERENCE TO RELATED APPLICATIONS

This application is a national phase under 35 U.S.C. §371 of PCT International Application No. PCT/SE2012/050851 which has an International filing date of Jul. 27, 2012, which claims priority to Swedish patent application number 1150724-1 filed Jul. 28, 2011 and U.S. provisional patent application No. 61/512,617 filed Jul. 28, 2011.

FIELD OF INVENTION

The present application relates to the field of immunohistochemistry as well as computer-based analysis of images. More specifically, the application provides a method of differentiating areas in a series of images.

BACKGROUND OF THE INVENTION

Analysis of a histological tissue sample is commonly used for diagnosis purposes, e.g. analysis of a breast tissue sample for diagnosing breast cancer, or for research purposes, e.g. to study inflammatory cell types in inflammatory conditions such as asthma, atherosclerosis, or inflammatory bowel diseases.

Immunohistochemistry (IHC), whereby a marker (i.e. an antigen) is detected by a antigen-specific antibody, is commonly used to identify cells in histological sections. Ideally, identification of a cell type can be obtained with detection of one cell-specific cell antigen. However, for several cell types combinations of several antigens must be analysed to for proper identification.

Any diseased tissue is typically associated with an altered cellular composition. For example, in inflamed airways in asthma there is an altered composition of the structural cells that build up the airways, such as epithelial cells, gland cells, blood vessel cells, nerves etc. In addition, several types of immune cells (i.e. leukocytes) infiltrate the inflamed airways.

In many diseases the pathological (i.e. destructive alterations) in the tissue is not caused by one cell type but rather a complex interaction between several cell types. Hence, when exploring a diseased tissue sample it is often desirable to study several cell populations and tissue structures. Information about the cellular content can be obtained by staining one cell type at the time in serially cut sections. Although this approach provides a good estimation of the content of several cell types in a tissue sample, it does not provide detailed information about the spatial relationship (i.e. physical relationship) between the analysed cell types.

In order to better explore how the composition of cells may define certain disease conditions, or study how cells interact and relate to each other inside a diseased tissue, it is desirable to develop means to visualize multiple cell types within the same three dimensional space, for example within one single tissue section.

With currently available IHC techniques it is possible to stain up to 4 cell types in one section using multiple-chromogen or multiple immunofluorescence techniques. In common practice, however, often only 2 cell types can be simultaneously detected due to lack of appropriate combinations of primary detection antibodies.

In order to increase the number of markers in one tissue section, new methodological approaches have been developed, such as the SIMPLE technique disclosed in WO 2010/115089 and the MELC technique (Schubert et al., Nature Biotechnology v. 24, pp. 1270-1278). Although powerful, these new types of techniques have primarily been developed for co-localization studies and either involve tissue-destructive procedures, procedures involving destruction of detection groups, or dependence of detection molecule-labeled primary antibodies, features that limit the number of cell markers that can be stained.

Since the above mentioned techniques were primarily developed for co-localization studies they do not deal with the fact that many identification markers may occasionally also be present on non-intended cell types.

Hence, there is a need for new technical approaches by which a large number of cell types can simultaneously be properly identified within the same physical space, such as one tissue section. Ideally, any such technique should be capable of analysing an entire large section of samples and providing detailed information about all marked individual cells such as their spatial coordinates in the tissue, their size and shape parameters etc.

SUMMARY OF THE INVENTION

In a first aspect, the present invention provides a method of differentiating areas in a series of N primary digital images of a tissue section wherein N is an integer >1, thereby creating a new image, said method comprising the steps of:

a) providing a series of N primary digital images comprising undetermined marker areas, wherein an image $I_{n+1}$ comprises at least the same amount of undetermined marker areas as a primary digital image $I_n$ for $2 \leq n \leq N$, wherein n is an integer;

b) evaluating every primary digital image $I_n$ for $1 \leq n \leq N$ according to predetermined selection criteria and defining image marker areas as undetermined marker areas fulfilling the predetermined selection criteria, and storing information about any such image marker area in or in connection/association with a resulting corresponding secondary digital image, thereby obtaining a series of N secondary digital images;

c) providing a new image $I_{new}$;

d) for every n for $2 \leq n \leq N$ of the series of secondary digital images obtained in step b), inserting new image marker areas in the new image $I_{new}$, said new image marker areas having the same shape and location as image marker areas present in image $I_n$ but not in image $I_{n-1}$, and said new image marker areas being identifiable in $I_{new}$ by a unique feature;

e) inserting new image marker areas in the new image $I_{new}$, said new image marker areas having the same shape and location as image marker areas present in image $I_1$, and said image marker areas being identifiable in $I_{new}$ by a unique feature.

Preferably, the step of providing a new image $I_{new}$ comprises providing an image of the tissue section.

Preferably, the new image $I_{new}$ is a copy of one of the images in said series of primary images.

Preferably, said unique feature in steps d) and e) is a feature that has a unique value for each n, $1 \leq n \leq N$.

Preferably, said unique feature is a general colour and said unique value of said unique feature is a specific colour associated with a particular cell marker.

Preferably, the predetermined selection criteria comprise a threshold for a visual property of an undetermined marker area.

In a second aspect, the invention provides a method for visualizing cell populations within a histological tissue section, said method comprising the steps of:

I) providing a tissue section that has been rendered ready for molecular staining;

II) providing a series of K particular molecular detection means for specifically binding to and detecting members of a predetermined series of K cell markers that may be present in the tissue section of step I), said molecular detection means being capable of generating formation of an initiable and detectable response, K being an integer >2;

III) for each particular molecular detection means k=1, 2, ..., K of step II) carrying out the following procedure:
1) contacting said tissue section of step I) with the particular molecular detection means resulting in specific binding to a particular member of said predetermined series of cell markers;
2) washing said tissue section in order to remove molecular detection means that has not been bound to any cell marker;
3) initiating response from molecular detection means that may have bound to cell markers of the tissue section thereby enabling detection of said molecular detection means; and
4) when said molecular detection means can be detected, scanning/imaging the tissue section in order generate a primary digital image $I_k$ that may contain one or more undetermined marker areas associated with generation of a detectable polymer;

whereby a series of K primary digital images $I_k$ for k=1, ..., K containing an increasing amount of undetermined marker areas is obtained;

IV) carrying out the method of the first aspect on the series of K primary digital images $I_k$ for k=1, ..., K obtained in step III), thereby generating an image $I_{new}$ visualizing said cell structures.

In a preferred embodiment of the method of the second aspect, said molecular detection means are a set of antibodies, preferably monoclonal antibodies or antibody fragments, wherein each antibody binds to a specific cell marker and wherein an enzyme has been has been conjugated to each antibody, said enzyme being capable of generating formation of a detectable polymer in presence of one or more suitable substrates, wherein items 1) and 2) of step III) are carried out in such a way that:
i) the tissue section of step I) is contacted with an antibody specifically binding to a particular member of said predetermined series of cell markers; said antibody being conjugated to an enzyme, said enzyme being capable of generating formation of a detectable polymer in presence of one or more suitable substrates;
ii) after step i) above, the tissue section is washed in order to remove unbound antibodies; and wherein item 3) of step III) is carried out in such a way that:
iii) after item 2) the tissue section is exposed to one or more suitable substrates for said enzyme, leading to formation of detectable polymers in case said particular member of said predetermined series of cell markers is present in said tissue section.

In another preferred embodiment of the method of the second aspect, said molecular detection means are a set of molecular complexes, where each complex comprises a first antibody, preferably a monoclonal antibody, binding to a specific cell marker, a second antibody or an antibody fragment, preferably a monoclonal antibody specifically bound to said first antibody, and an enzyme conjugated to said second antibody, said enzyme being capable of generating formation of a detectable polymer in presence of one or more suitable substrates, wherein items 1) and 2) of step III) is carried out in such a way that:
i) the tissue section of step I) is contacted with a first antibody specifically binding to a particular member of said predetermined series of cell markers;
ii) after step i) above, the tissue section is washed in order to remove unbound antibodies;
iii) after step ii) above, the tissue section is contacted with a second antibody specifically binding to said first antibody, said second antibody being conjugated to an enzyme, said enzyme being capable of generating formation of a detectable polymer in presence of one or more suitable substrates; and
iv) after step iii) above, the tissue section is washed in order to remove unbound antibodies; and wherein item 3) of step III) is carried out in such a way that:
v) after item 2) the tissue section is exposed to one or more suitable substrates for said enzyme, leading to formation of detectable polymers in case said particular member of said predetermined series of cell markers is present in said tissue section.

Preferably, said enzyme is chosen from the group of alkaline phosphatase and peroxidase, In one embodiment, said peroxidase is horseradish peroxidase.

Preferably, said substrate is selected from the group of 3,3'-diaminobenzidine, Ferangi Blue, Vulcan Fast Red, Vina green, and aminoethyl carbazole (AEC). Vina green is an example of a substrate generating a polymer that is at least partially water soluble under certain conditions. Aminoethyl carbazole (AEC) is an example of a substrate generating polymers that are at least partially soluble in lower alcohols such as ethanol, under certain conditions. 3,3'-diaminobenzidine, Ferangi Blue, and Vulcan Fast Red are examples of substrates generating insoluble polymers.

It is understood that different substrates and/or enzymes may be utilized during the execution of the method. For example, diaminobenzidine may be utilized as substrate in the first execution of item 2), and Vulcan Fast Red may be utilized as substrate in a subsequent execution of item 2).

In yet another preferred embodiment of the method of the second aspect, said molecular detection means are a set of molecular conjugates comprising a recognizing part bound to a detecting part, wherein said recognizing part is capable of specifically binding to a particular member of said predetermined series of cell markers, said recognizing part being selected from the group of an antibody and a nucleic acid molecule, said detecting part being a fluorochrome, said fluorochrome being capable of emitting radiation of a particular wave length after exposure to initiating radiation different from said emitted radiation wherein item 3) of step III) is carried out in such a way that the tissue section and any molecular detection means that have been bound thereto are exposed to initiating radiation leading to emission of radiation of a particular wave length in case said particular member of said predetermined series of cell markers is present in said tissue section; and wherein item 4) of step III) is carried out when said radiation of a particular wave length is emitted.

In one embodiment, the antibody may be a polyclonal antibody, a monoclonal antibody or fragments thereof.

In one embodiment, the nucleic acid molecule may be an RNA molecule or a DNA molecule.

In yet another preferred embodiment of the method of the second aspect, a substrate generating at least partially soluble polymers as detectable polymers is used.

In one embodiment, the detectable polymers may be Vina green or aminoethyl carbazole (AEC).

In one embodiment, the method of the second aspect further comprises the steps of V) washing said tissue section in order to remove the soluble detectable polymers; and VI) repeating steps II-IV with a new series of molecular detection means. This embodiment is useful when presence of a large amount of cell markers is to be assessed.

In a third aspect, the present invention provides a method for visualizing the three-dimensional distribution of multiple cell populations and cell structures within the same three-dimensional space in a histological sample, comprising the steps of:

A) providing a tissue sample, and cutting said sample in a plurality of originally superposed tissue sections in previously known manner;

B) carrying out the method according to the second aspect for all tissue sections obtained in step A); and C) superposing the images obtained in step B) according to known principles, thereby obtaining a three-dimensional visualization of the three-dimensional distribution of multiple cell populations and cell structures within the same three-dimensional space in a histological sample.

DEFINITIONS

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice of the present invention, the preferred methods and materials are described herein. As used herein, each of the following terms has the meaning associated with it in this section. Specific and preferred values listed below for radicals, substituent, and ranges are for illustration only; they do not exclude other defined values within defined ranges for the radicals and substituent.

By cell marker is meant a specific structure that, depending on cell type, may occur more or less specifically, often on the surface of a cell of the cell type, but sometimes also within the cell. Typically, a cell marker is a receptor capable of binding specifically to a particular target molecule. The cell marker may be a protein, a glycoprotein, or a carbohydrate, a nucleic acid, a lipid or another type of naturally occurring biological molecule. The skilled person knows about such cell markers and cell types on which they occur. Presence of one or more such cell markers may indicate that the cell belongs to a certain class or type of cells.

By molecular detection means is meant a bi-functional aggregate or conjugate comprising a first part capable of specific binding to a particular cell marker, and a second part capable of generating a detectable response. Many different types of molecular detection means could be used in the present invention.

Typically, said first part capable of specific binding to a particular cell marker could be an antibody or a fragment thereof such as a Fab fragment, or a nanobody, or a nucleic acid molecule such as a DNA molecule or an RNA molecule or a nucleic acid derivative such as PNA. Typically, said second part capable of generating a detectable response could be an enzyme, or a chemical compound capable of generating some kind of detectable signal, such as a fluorochrome, when induced by a specific action.

A molecular detection means could, in its simplest embodiment, be comprised of a first part such as an antibody or a nucleic acid molecule to which the second part such as an enzyme or a fluorochrome has been bound. Alternatively, a suitable molecular detection means could be a complex comprising a first entity, typically a monoclonal or a polyclonal antibody specifically binding to a particular cell marker, a second entity, typically a monoclonal or a polyclonal antibody, specifically binding to the first entity, and a third entity bound to the second entity, where said third entity could be an enzyme or a chemical compound capable of generating some kind of detectable signal, such as a fluorochrome, when induced by a specific action.

By detectable response is meant a response that could be detected in a scanning/imaging step in such a way that the response could be located within the image produced by said scanning/imaging step.

In one embodiment, the detectable response is formation of an opaque and/or coloured polymer. Such polymers could be formed by contacting certain enzymes which are part of a molecular detection means with specific substrates under suitable conditions. Examples of suitable enzymes are alkaline phosphatase and peroxidase, such as horseradish peroxidase. Examples of suitable substrates for such enzymes are 3,3'-diaminobenzidine, Ferangi Blue, Vulcan Fast Red, aminoethyl carbazole (AEC), and Vina green.

In another embodiment, the detectable response is emission of radiation of a certain wave length, such as radiation emitted by a flourophore after excitation.

In another embodiment, different forms of detectable responses are utilized within a single execution of the method.

By primary digital image is meant a digital image that has been obtained by direct digitalization (e.g. slide scanning or micro-photography) of a tissue section. No additional adaptation, editing or evaluation of the image has been made. Such an image should be considered as raw source data.

By secondary digital image is meant an image that has been obtained by some kind of digital editing or evaluation of a primary digital image. A secondary digital image can be obtained by, e.g., editing and/or evaluating a primary digital image. The primary digital image is thereby redefined as a secondary digital image.

By undetermined marker area is meant a detectable element or structure in a primary digital image of a tissue section. An undetermined marker area may indicate presence of naturally occurring opaque structures and elements, such as blood vessels and cell organelles, in the tissue section or endogenous pigment in tissue elements. It may also indicate presence of a detectable marker means, such as a detectable polymer or a fluorochrome, which in turn indicates presence of a cell marker that has been detected by a molecular detection means generating production of such a polymer or a emission of detectable radiation after excitation.

By image marker area is meant an area in a secondary digital image of a tissue section. An image marker area corresponds to the whole or a part of an undetermined marker area in a primary digital image. An image marker area is obtained by evaluating a primary digital image, and in particular undetermined marker areas of a primary digital image, and defining image marker areas according to specified selection criteria. A secondary digital image containing image marker areas also contains or is connected/associated with information about each image marker area.

By shape of a marker area is meant the shape of the perimeter of the area. There are a number of known methods for determining the shape of areas in a digital image, included in software such as ImageJ provided by National Institute of Health (NIH) and Photoshop® provided by Adobe®.

By location of an area in an image is meant which position the area has in the image. By the same location for an area in different images is meant
- the same position in relation to a coordinate system equally constructed for the images; or
- a corresponding position in terms of the depicted subject, if the two images depict the same subject.

By selection criteria is meant selection criteria which may be used to evaluate a primary digital image in order to define image marker areas. The criteria may for example comprise thresholds for colour and/or intensity for one pixel or a group of adjacent pixels in an image. The selection criteria could comprise shape criteria, colour criteria, size criteria or other types of criteria which will be described in the detailed description and which will be appreciated by the skilled person. Furthermore, it is natural for the skilled person carrying out the present method to optimize parameters and selection criteria for particular circumstances.

By unique feature is meant a characteristic of one or more image marker areas identified as a particular type differentiated from other image marker areas. The unique feature may comprise a visual feature such as a colour, symbol, shape, label or be a digital association between the image marker areas and their particular type (for example a primary cell type). The association is stored in, e.g., a database. The unique feature may be any other suitable feature for distinguish a marker area of a certain type in a digital image from marker areas of other types.

Such a feature may also be further subdivided into unique values. For instance molecular detection means for detecting similar but different cell markers could be identifiable by a unique feature (such as a colour) and each individual cell marker could be identified by a unique value (such as a nuance of said colour).

BRIEF DESCRIPTION OF THE DRAWINGS

The present invention will now be described with reference to the enclosed figures, in which.

DETAILED DESCRIPTION OF THE PRESENT INVENTION

Figure 1:
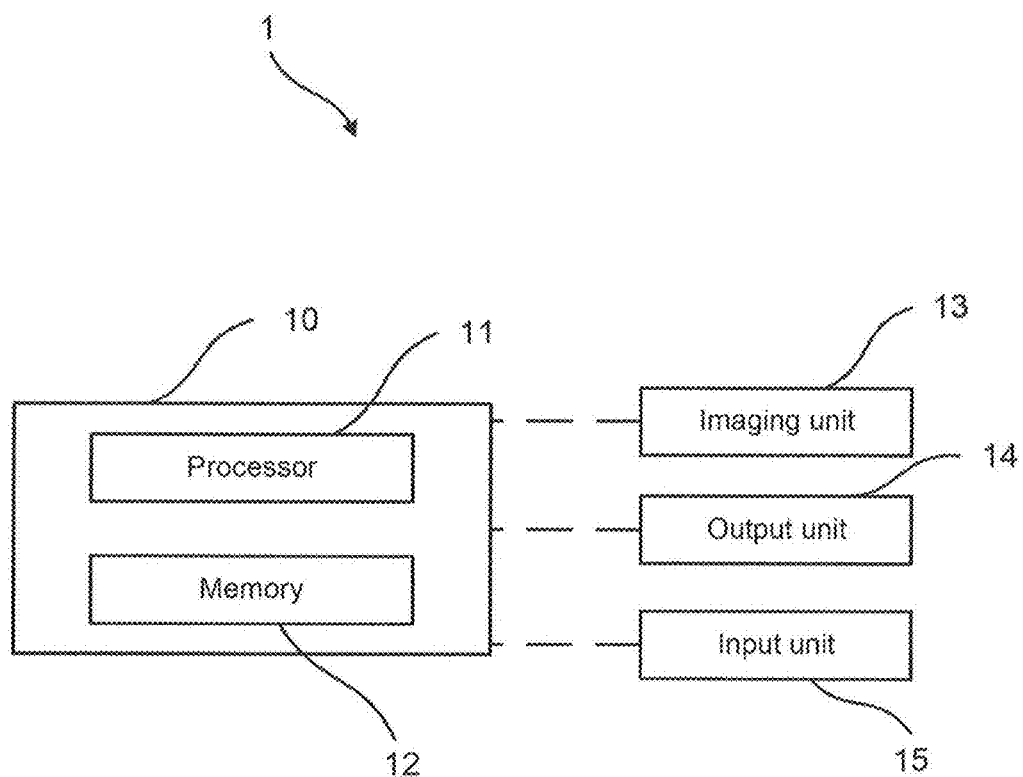
FIG. 1 illustrates an apparatus executing the method according to the present invention.

The present invention relates to a technique referred to as Exclusion and Subtraction-based Multiple Staining, abbreviated ESMS. The technique renders it possible to provide a high resolution image of a histological tissue section in which a plurality of cell types and tissue structures could be identified. Spatial analysis methods for the plurality of cells and cell types can be applied to provide useful spatial information for a tissue section which cannot be provided with known techniques. The present invention is based upon the realization that such information may be of great value when analyzing tissue sections. The inventor of the present invention has come up with a technology for providing images of tissue section comprising spatial information in a simple and efficient manner. The technology also renders it possible to provide high resolution image data in three dimensions which facilitates studies of complex interactions of cells and tissue structures within the same three-dimensional space in a tissue sample.

The method provides composite images of tissue sections which, apart from visualizing multiple marker distribution within the same section, provide the basis for extracting information that can be used for advanced mathematical analysis of the distribution patterns of structures and elements in the tissue section. Examples of such information are relationship between elements, such as cells, or information about structures in the sections revealed by the conventional blue background staining such as histological structures or focal areas of tissue damages, hypotrophy, tissue remodelling etc.

The present invention could be carried out starting from any tissue sample that could be used for detecting molecules or structures in histological studies. The examples of molecular detection in the present application relates to immunohistological methods but other means of staining molecules could also be used; for example in situ hybridization, non-antibody dependent ligand binding techniques, or enzyme histochemistry. Typically, prior to molecular detection, a tissue sample is immersed into fixative (e.g. 4% buffered formaldehyde, pH 7.6) overnight followed by dehydration in a series of solutions with increasing concentration of alcohol (EtOH) and final immersion into xylene. After the dehydration step, the dehydrated specimen is embedded in paraffin and paraffin sections are generated with a routine paraffin-cutting microtome. The paraffin sections are mounted on standard microscope glass slides and stored at 4° C. until use. The skilled person is well acquainted with different suitable fixatives and fixation processes for different kinds of tissue sections and he may therefore use other such methods than the method mentioned above, including cryo sectioning techniques.

Before the actual immunohistochemistry (abbreviated IHC), the paraffin sections are deparaffinized and typically subjected to heat-induced or enzymatic antigen retrieval. Such processes are also well-known to the skilled person.

The tissue section obtained after deparaffinization and heat-induced antigen retrieval then is subjected to further specific detection. It is essential to be able to determine cell types and tissue types comprised in such a tissue section. In order to be able to do that, the occurrence of some specific cell markers in the tissue section is checked.

Table 1 below lists some examples of immune cell markers which are suitable for use in the present invention, and cells expressing them:

TABLE 1

Cell markers for IHC detection of cells in histological sections

| Cell marker | Primary cell |
| --- | --- |
| CD20 | B-lymphocytes |
| CD8 | T lymphocytes |
| ECP (EG2) | Eosinophils |
| CD11c | Myloid dendritic cells, Macrophages |
| Tryptase | Mast cells |

TABLE 1-continued

Cell markers for IHC detection of cells in histological sections

| Cell marker | Primary cell |
|---|---|
| CD68 | Macrophages/monocytes (and occasional neutrophils) |
| MPO | Neutrophils |
| CD163 | Most tissue Macrophages (but not in follicular macrophages) and Langerhan cells |
| CD123 | Plasmacytoid dendritic cells, macrophages/monocytes, neutrophils, eosinophils |
| CD68 | Macrophages/monocytes, neutrophils, basophils, large lymphocytes |
| CD45 | All leukocytes |

When determining presence of a cell marker in a tissue section in accordance with the present invention, the tissue section is exposed to a molecular detection means specifically binding to said cell marker.

The first part of a molecular detection means could be a natural ligand associated with the cell marker to which it specifically binds. Alternatively, and preferably, the first part is an antibody, and often a monoclonal antibody or a fragment thereof.

The second part of a molecular detection means typically comprises an enzyme capable of generating a detectable polymer in presence of a suitable substrate. Non-limiting examples of such enzymes are alkaline phosphatase and peroxidases, such as horseradish peroxidase. Peroxidases, for example, generate a detectable brown-coloured polymer in presence of the peroxidase substrate 3,3'-diaminobenzidine (abbreviated DAB), and alkaline phosphatases generates detectable polymers in presence of Ferangi Blue and Vulcan Fast Red. Another non-limiting example of a substrate generating an at least partially soluble polymer is Vina green. The resulting polymer from Vina green is soluble in water under certain conditions. Another non-limiting example of a substrate generating an at least partially soluble polymer is aminoethyl carbazole (AEC). The resulting polymer from aminoethyl carbazole is soluble in lower alcohols, such as ethanol, under certain conditions. Other substrates may generate polymers which are soluble by other fluids.

The skilled person is able to find other suitable such enzymes and substrates, or will know also know that, instead of enzymes, fluorochromes can be used to visualize marker molecules by immunofluorescence microscopy.

The molecular detection means could be provided as a single conjugate, typically comprising an antibody binding to a cell marker and an enzyme such as a peroxidase or alkaline phosphatase, where the antibody and the enzyme is joined by a chemical linking group. Alternatively, and more preferably, the molecular detection means is provided as a molecular aggregate comprising a first monoclonal or polyclonal antibody or a fragment thereof and a second antibody or fragment thereof chemically linked to an enzyme such as alkaline phosphatase or a perpoxidase. The second molecular antibody or fragment thereof specifically binds to the first primary antibody or fragment thereof, thereby forming the molecular aggregate.

The method of the invention provides a way of differentiating elements and structures in a tissue section and accordingly a series of such molecular detection means are used. Depending on organ or tissue type from which the tissue section was taken as well as basic knowledge of cell markers from different cell types and tissues, the skilled person is able to design a suitable series of molecular detection means that is to be used in differentiating cells and tissue types in the tissue section.

It is understood that different types of molecular detection means may be combined within a single execution of the method of the invention. This may be advantageous since the elements and structures may more easily be differentiated from each other and its surroundings during the image analysis of the primary digital images.

According to the present invention, the following detection process for the tissue section is run with one molecular detection means of said series of molecular detection means at a time:

1) contacting said tissue section of step I) with the particular molecular detection means resulting in specific binding to a particular member of said predetermined series of cell markers;
2) washing said tissue section in order to remove molecular detection means that has not been bound to any cell marker;
3) adding a suitable substrate resulting in generation of a detectable polymer;
4) washing the tissue section in order to remove remaining substrate; and
5) scanning/imaging the tissue section in order to generate a primary digital image that may contain one or more undetermined image marker area or areas associated with generation of a detectable polymer.

Figure 8:
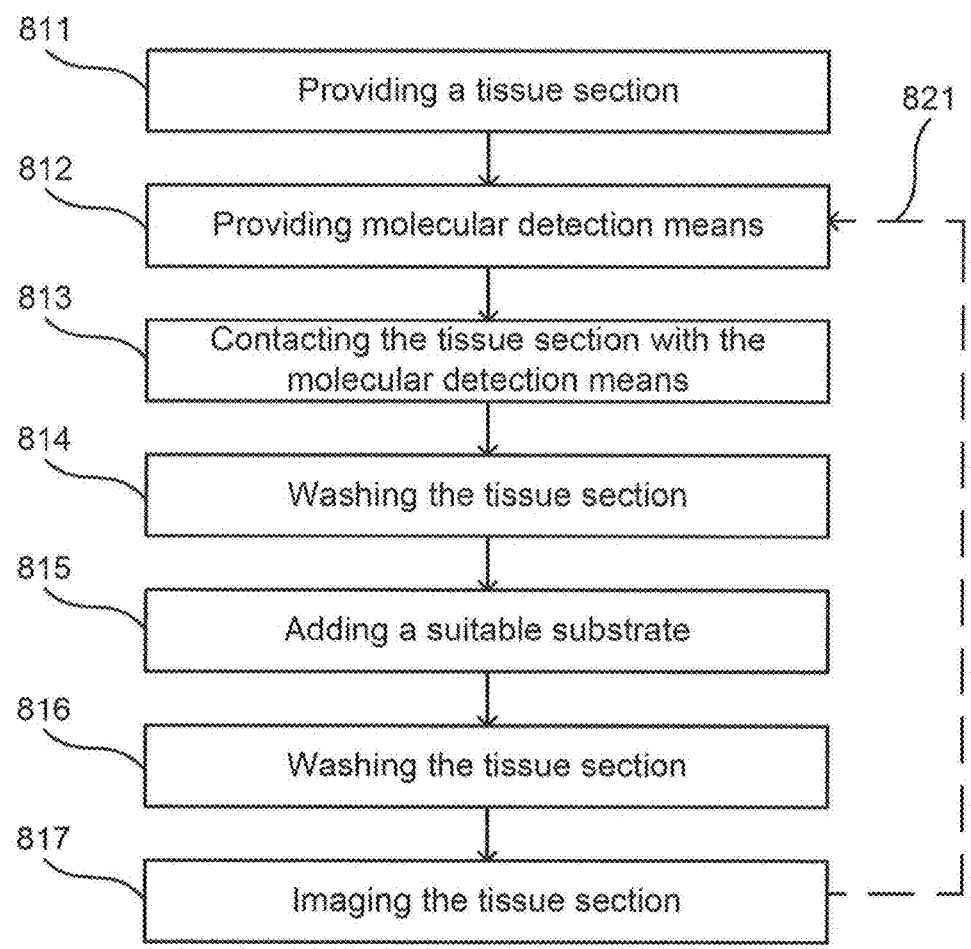
FIG. 8 illustrates a detection process according to the present invention.

The detection process is illustrated as a method in FIG. 8, where the method comprises the steps of:
providing (811) a tissue section;
providing (812) molecular detection means;
contacting (813) the tissue section with the molecular detection means, as disclosed in step 1) above;
washing (814) the tissue section, as disclosed in step 2) above;
adding (815) a suitable substrate, as disclosed in step 3) above;
washing (816) the tissue section, as disclosed in step 4) above; and
imaging (817) the tissue section, as disclosed in step 5) above.

Figure 4:
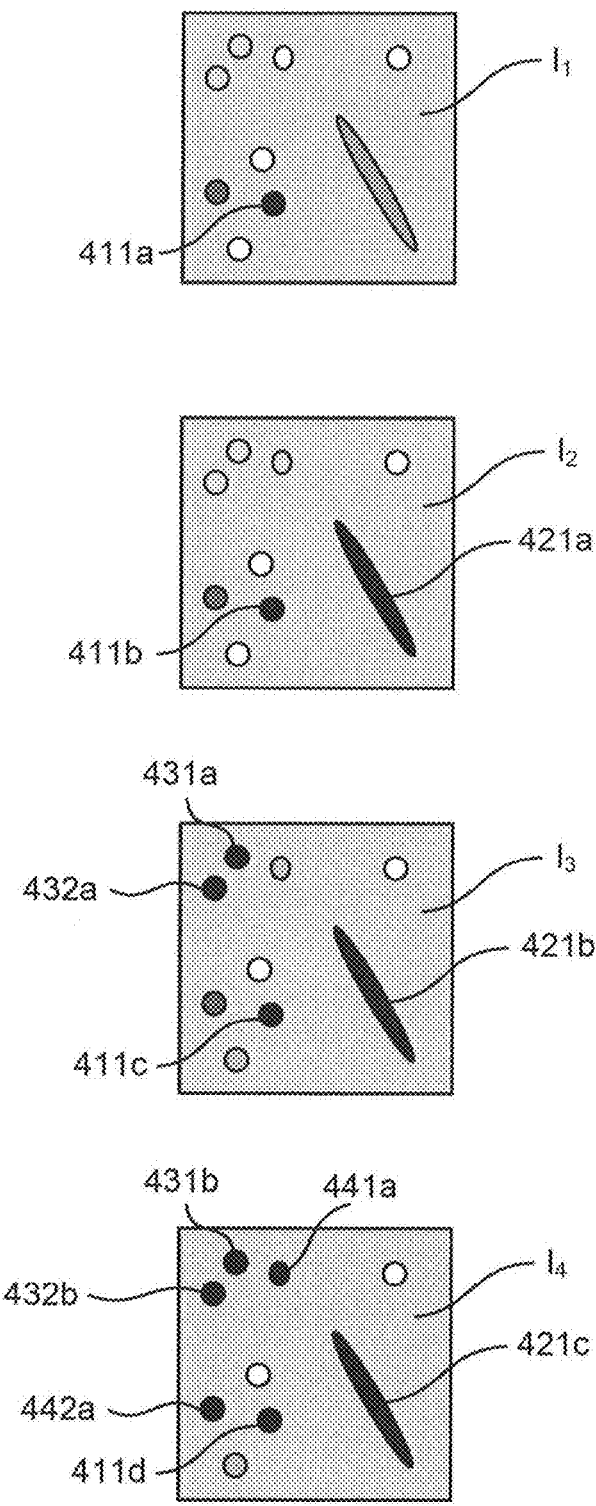
FIG. 4 illustrates a series of images of a tissue section.

By repeating steps 812-817, as indicated by 821, for different molecular detection means and substrates suitable for different primary cell types, a series of images is provided comprising the images generated in step 817. An example of such a series of images is illustrated by FIG. 4, which will be described more in detail later.

The scanning/visualization step included as step 5 in the detection process could be carried out with any commercially available slide scanning equipment intended for tissue section, a microscope equipped with a digital camera or a whole side scanner robot.

The repeated steps 812-817 may be carried out in an automated manner. As a non-limiting example, a so called slide chamber technique may be utilized for the repeated steps. In the slide chamber technique, the tissue section is arranged in a micro compartment through which molecular detection means, washing fluids etc. may pass. The different steps 812-817 may thus be carried out without the need for moving the tissue sample to and from the imaging means. Thus, the primary images may be provided having the same image characteristics, such as disclosing the exact same part of the tissue sample and having the same depth of focus. Also, the method may be carried out in a more time-efficient manner and without the need for manual handling or interaction. The skilled person realizes that the method may also be carried out by means of other automated techniques.

When the detection process has been carried out for all molecular detection means of the series, a series of images is obtained where there are an increased amount of coloured spots. The first images corresponding to treatment with a small amount of molecular detection means may only comprise a few sports. The last image on the other hand should comprise a multitude of spots and it is also possible that some spots have fused and expanded into large coloured areas.

In one embodiment, the series of images may be provided by imaging a tissue section according to the following detection process:
1) contacting the tissue section with a particular molecular detection means resulting in specific binding to a particular member of said predetermined series of cell markers;
2) washing the tissue section in order to remove molecular detection means that has not been bound to any cell surface marker;
3) adding suitable detecting reagents such as a secondary antibody that recognizes the primary detection antibody. Typically, the secondary antibody is labeled with an enzyme, for example peroxidase.
4) washing the tissue section in order to remove molecular detection means that has not been bound to any cell surface marker;
5) adding enzyme substrate resulting in generation of a detectable polymer;
6) washing the tissue section in order to remove remaining substrate; and
7) scanning/imaging the tissue section in order to generate a primary digital image that may contain one or more undetermined marker areas associated with generation of a detectable polymer.

As indicated in Table 1 above, some cell surface markers are associated with a restricted range of cells whereas other markers occur in a broader range. In Table 1, it can for instance be noted that CD20 is mainly associated with B lymphocytes. In contrast, CD123 is associated with a substantially larger range of cell types. When setting up said series of molecular detection means, it is advantageous to include molecular detection means specific for only a small amount of cell types, and preferably only one cell type, in the beginning of the series of molecular detection means. Then, confounding cell types and structures associated and detected with the first molecular detection means can be ruled out when determining cell types and structures using more general molecular detection means later on and the accuracy of cell identification is increased. Based on this information, it is easy to the skilled person to conceive suitable series of molecular detection markers.

It has turned out that the following examples of series of molecular detection means binding to cell surface markers provide good results:

A: Simultaneous detection of 10 leukocyte populations with improved cell identification

| Cell marker | Primary cell | Comment |
|---|---|---|
| CD20 | B lymphocytes | |
| CD4 | Th-lymphocytes | |
| CD8 | Tct-lymphocytes | |
| BB1 | Basophils | |
| EG2 | Eosinophils | |

-continued

| Cell marker | Primary cell | Comment |
|---|---|---|
| MPO | Neutrophils | |
| Tryptase | Mast cells | |
| CD68 | MQ/monocytes (but also occasional neutrophils) | Confounding neutrophils have already been stained and identified in a previous step and are both physically and digitally excluded in the CD68 staining cycle |
| CD11c | Myloid DC (but also on macrophages) | Confounding macrophages have already been identified. |
| CD123 | Plasmacytoid DC (but also on macrophages and neutrophils and eosinophils) | Confounding macrophages and neutrophils have already been identified and can be excluded |

B: Simultaneous identification of multiple histological tissue compartments

| Cell surface marker | Tissue compartment/structure |
|---|---|
| Neuron Specific Enolase or the nerve marker PGP | Nerves |
| Alpha smooth muscle actin | Smooth muscle tissue |
| DP-40 (prox-1) | Lymphatic vessles |
| Cav-1 (or CD31) | Blood vessels |
| Cytokeratin | Epithelial and glandular tissues |
| Viementin | Fibroblasts (when applied after leucocyte package) |

C: Analysis of leucocyte-infiltrating patterns in relation to tissue areas of damage/repair and major histological tissue compartments of the airways

| Cell surface marker | Primary cell/structure |
|---|---|
| CD20 | B lymphocytes |
| CD3 | T lymphocytes |
| BB1 | Basophils |
| EG2 | Eosinophils |
| MPO | Neutrophils |
| Tryptase | Mast cells |
| CD68 | Macrophages |
| Pan-Cytokeratin | Epithelial tissue |
| Von Willebrand factor | Blood vessels |
| Alpha-SMA | Smooth muscle tissue |

E: Improved identification of tissue dendritic cell (DC) populations

| Cell surface marker | Primary cell/structure | Advantage/extra info |
|---|---|---|
| CD21 | Follicular DCs | |
| CD68 | MQ/monocytes | Masking of confounding MQs and monocytes |
| BDCA-3 | BDCA3$^+$ subset of myloid dendritic cells | New image markers represent CD68-negative, BDCA-3+ dendritic cells |
| CD11c | BDCA3-negative Myloid dendritic cells | New image represent CD68$^-$, BDCA-3−, CD11c$^+$ DCs |

-continued

| Cell surface marker | Primary cell/structure | Advantage/extra info |
|---|---|---|
| CD123 | Plasmacytoid DC | * CD68$^-$, CD123$^+$ DCs |
| Langerin (CD207) | Mucosal DC pop1 | * CD68$^-$, CD11c$^-$, CD207$^+$ DCs |
| CD1a | Mucosal DC pop2 | * CD68$^-$, CD207$^-$, CD1a$^+$ |

* Only positive and negative markers relevant for improved cell identification are outlined (technically, cells that are stained in any step is negative for all markers used in the previous staining cycles)

The core part of the present invention relates to how the obtained series of images is analyzed and transformed into new edited images and three-dimensional depictions comprising added information for visualizing multiple cell populations and tissue structures and their spatial relationship within the same two or three-dimensional space.

The image analysis part of the present invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

FIG. 1 is a block diagram illustrating a device, generally given by 1, for differentiating areas in a series of images according to the present invention. The device comprises an apparatus 10 which comprises a processor 11 and a memory 12. The apparatus 10 could be part of a computer. The processor 11 may be arranged to register shape and location of areas in an image. The shape and location may be stored associated with or in connection to the image, e.g. in a database in the memory 12. The processor 11 may further be arranged to evaluate an image in order to identify image marker areas according to predetermined selection criteria. The processor 11 may furthermore be arranged to compare two images and identify image marker areas present in one of the images but not in the other. The processor 11 may also be arranged to insert new image marker areas having the same shape and location as identified image marker areas in another image, wherein the inserted markers are identifiable in the other image by a unique feature.

In one embodiment, an imaging unit 13 is connected to the apparatus 10. The imaging unit 13 is for example a digital CCD camera or a digital scanner such as a slide scanner. Alternatively, instead of having an imaging unit 13 connected to the apparatus 10, images can be provided to the apparatus 10 by connecting a storage medium, such as a USB memory, comprising the images. The provided images may be stored in the memory 12.

An output unit 14 can be connected to the apparatus 10 in order to provide output from the apparatus 10 to a user. The output unit 14 is, e.g., a display such as a computer screen or a mobile phone display. The output is preferably in form of a software interface, i.e. a graphical user interface for displaying an image. The apparatus 10 preferably further comprises an input unit 15 for receiving user input. Typical examples of an input unit 15 are a key pad or a data connection means.

Figure 2A:
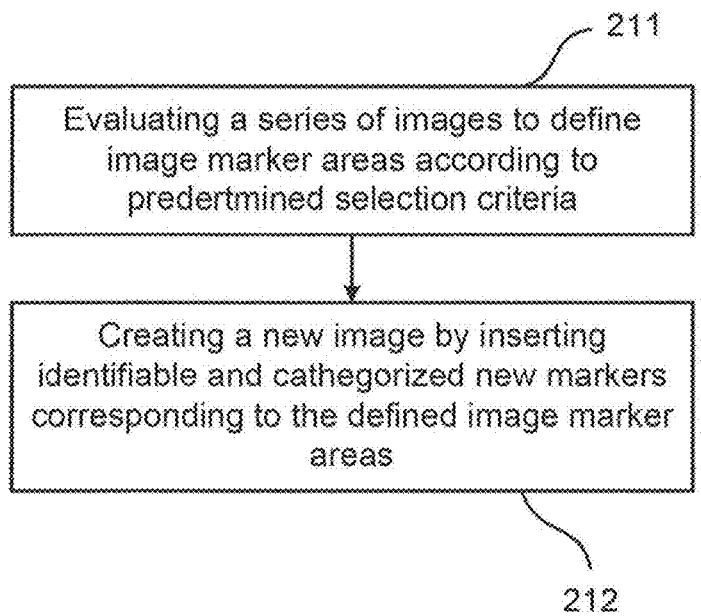
FIGS. 2a-b illustrate a method for differentiating marker areas in a series of images according to the present invention.

FIG. 2a generally illustrates a method according to the present invention for differentiating marker areas in a series of images which may be executed in the apparatus 10. The method comprises the following steps:

A first step 211 of evaluating a series of primary digital images in order to define image marker areas according to predetermined selection criteria.

A second step 212 of creating a new image, based on the series images, by inserting new markers corresponding to the defined image marker areas in the previous step 211, such that the markers are identifiable.

Figure 2B:
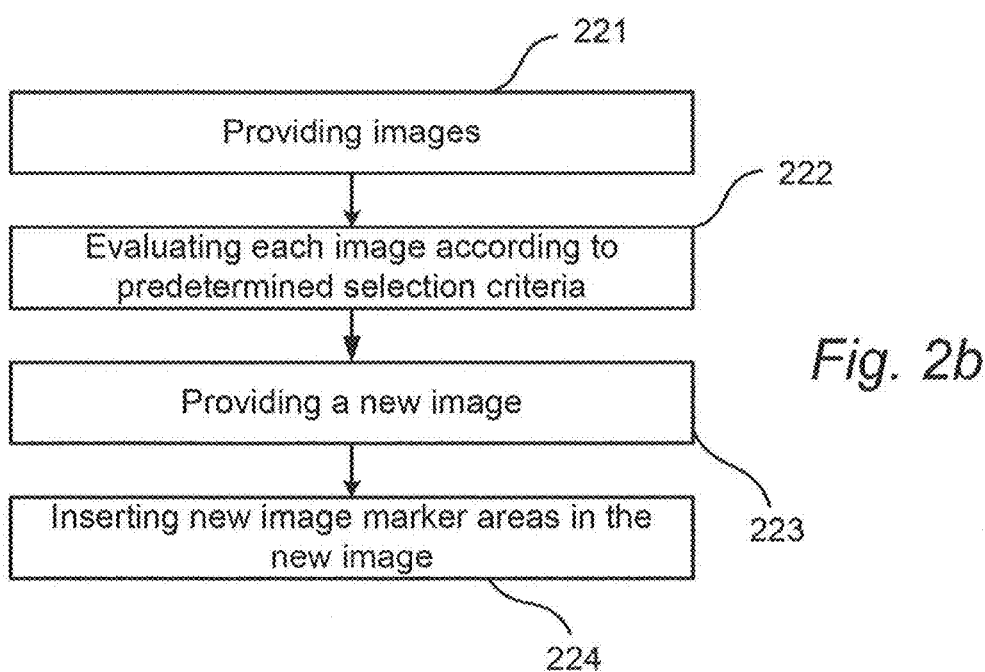

The method will now be described in detail with reference to FIGS. 2b and 1.

Step 221 comprises providing a series of N primary digital images $I_1, I_2, \ldots, I_N$ where N is an integer equal to or larger than 2. The images is provided by the imaging unit 13 or by a storage unit (not shown) connected to the apparatus 10.

The series of N primary digital images is provided by imaging a tissue section according to the following detection process (also disclosed above and as illustrated by FIG. 8):

1) contacting the tissue section with a particular molecular detection means resulting in specific binding to a particular member of said predetermined series of cell markers;
2) washing the tissue section in order to remove molecular detection means that has not been bound to any cell marker;
3) adding a suitable substrate resulting in generation of a detectable polymer;
4) washing the tissue section in order to remove remaining substrate; and
5) scanning/imaging the tissue section in order to generate a primary digital image that may contain one or more undetermined marker areas associated with generation of a detectable polymer.

The detection process is repeated a desired number of times. Step 5 (corresponding to step 817 in FIG. 8) generates a primary digital image every process cycle. Hence, N cycles generates a series of N images.

The process generates images where image $I_{n+1}$ comprises at least the same amount of undetermined image marker areas as image $I_n$ for $2 \leq n \leq N$, wherein n is an integer. Thereby, the series of images comprises an increasing amount of undetermined marker areas where the image $I_N$ comprises the largest amount of undetermined marker areas and $I_1$ comprises the least amount of undetermined marker areas.

Next, step 222 comprises evaluating every image $I_n$ for $1 \leq n \leq N$ according to predetermined selection criteria, and defining image marker areas. In particular, the undetermined marker areas are evaluated. Areas in the image that fulfill the predetermined selection criteria are defined as image marker areas. As already mentioned in the definitions section above, there could typically be size criteria, shape criteria and colour criteria. The selection criteria greatly influence the outcome of the evaluation process. For instance, a comparably high threshold level regarding size leads to may lead to clearer images that are easy to assess but there is always a risk that relevant structures having a smaller size will not be detected. When deciding selection criteria it is therefore preferred to consider data regarding cells and cell structures normally present in a section of the tissue type that is about to be studied. The skilled person has this knowledge.

An area comprises one or more pixels. An area may furthermore be defined as a plurality of adjacent pixels in the image. How an area is defined could be part of the predetermined selection criteria. The criteria could for example comprise a criterion that only areas of more than twenty pixels should be defined as image marker areas. Another criterion could be that the pixels forming the area should resemble a particular shape. The step 222 corresponds to the step 211 in FIG. 2a.

Step 223 comprises providing a new secondary digital image $I_{new}$. The new image may depict the same subject as the series of images. In particular, the new image may be a copy of one of the primary digital images in the series of images. In such an embodiment, $I_{new}$ may be created by copying one of the images in the series of images.

Advantageously, the new image depicts the tissue sample as close to the original tissue sample as possible, i.e. before any detection process cycle. This may be achieved by imaging the tissue section, thus creating an image $I_0$, before the first detection process cycle is performed. In such an embodiment, the image $I_0$ may be provided in a step before the step 221 of providing the series of images.

Alternatively, the new image may be a blank image, i.e. without any content. A blank image can be created by the processor 11. By blank image is meant, e.g., an image wherein all pixel values, e.g. RGB value, are set to zero.

In another alternative embodiment, the new image is provided by capturing an image after an initial staining of the tissue sample with a standard counter stain like hematoxylin, or any other stain that provides valuable information about the tissue background and do not interfere with the subsequent immunohistochemistry and detection steps.

It should be noted that the new image may be provided from, e.g., an imaging unit or from a memory unit and that the method is not limited to either one of these alternatives.

New image marker areas may be inserted in $I_{new}$ in any order.

It should be noted that the step 223 of providing the new image $I_{new}$ may be executed before the step 222 of evaluating every image or before the step 221 of providing the series of image, i.e. the step of providing the new image is not dependent on its previous steps.

Step 224 comprises inserting new image marker areas, in the new image $I_{new}$. For every image $I_n$ for $2 \leq n \leq N$, new image marker areas are inserted in $I_{new}$ with the same shape and location as image marker areas present in image $I_n$ but not in image $I_{n-1}$. This is achieved by comparing each image $I_n$ with is subsequent image $I_{n-1}$ and identifying image marker areas present in $I_n$ but not in $I_{n-1}$. The evaluation does not need to be performed for n in a certain order and can in fact be performed in whichever order it is found suitable. What is important, however, is that the order of images within the series is kept and that only image marker areas present in image $I_n$ but not in image $I_{n-1}$ are identified.

How to compare and insert image marker areas with the same shape and location in the new image may be performed in many ways, all well known to the person skilled in the art. Examples are storing shape and/or location parameters in a database and; using a copy-paste function in an image editor software; etc. The step 224 will be further explained in connection to FIGS. 4-5.

The inserted image marker areas in $I_{new}$ are furthermore made identifiable in $I_{new}$ by a unique feature, in particular a unique value of a unique feature. The identifiable feature is a feature not originally present in $I_{new}$ and could for example be a colour. In this case, a unique value of a colour could be a particular and unique nuance. What is important is that the value is unique for the particular molecular detection means used in the detection process cycle generating image $I_n$ and consequently the corresponding element or structure. A purpose of the unique feature/value is that they differentiate different image marker originating from different cycles of detection processes and hence, different molecular detection means for different elements/primary cells and structures of the tissue section. In one embodiment, the unique feature is visual markers in the new image. In one embodiment, the unique feature is a general colour and the unique value of the unique feature is a specific colour associated with a particular cell marker.

In another embodiment, the unique feature for image marker areas originating from $I_n$ is a digital association/connection between image marker areas and the corresponding elements and/or structures aimed to mark in cycle n of the detection process. The association/connection is stored in association/connection to the image $I_n$, such as in an associated database in the memory 12.

The step 211 of evaluating a series of images in order to define image marker areas according to predetermined selection criteria will now be described with reference to FIG. 3.

Figure 3:
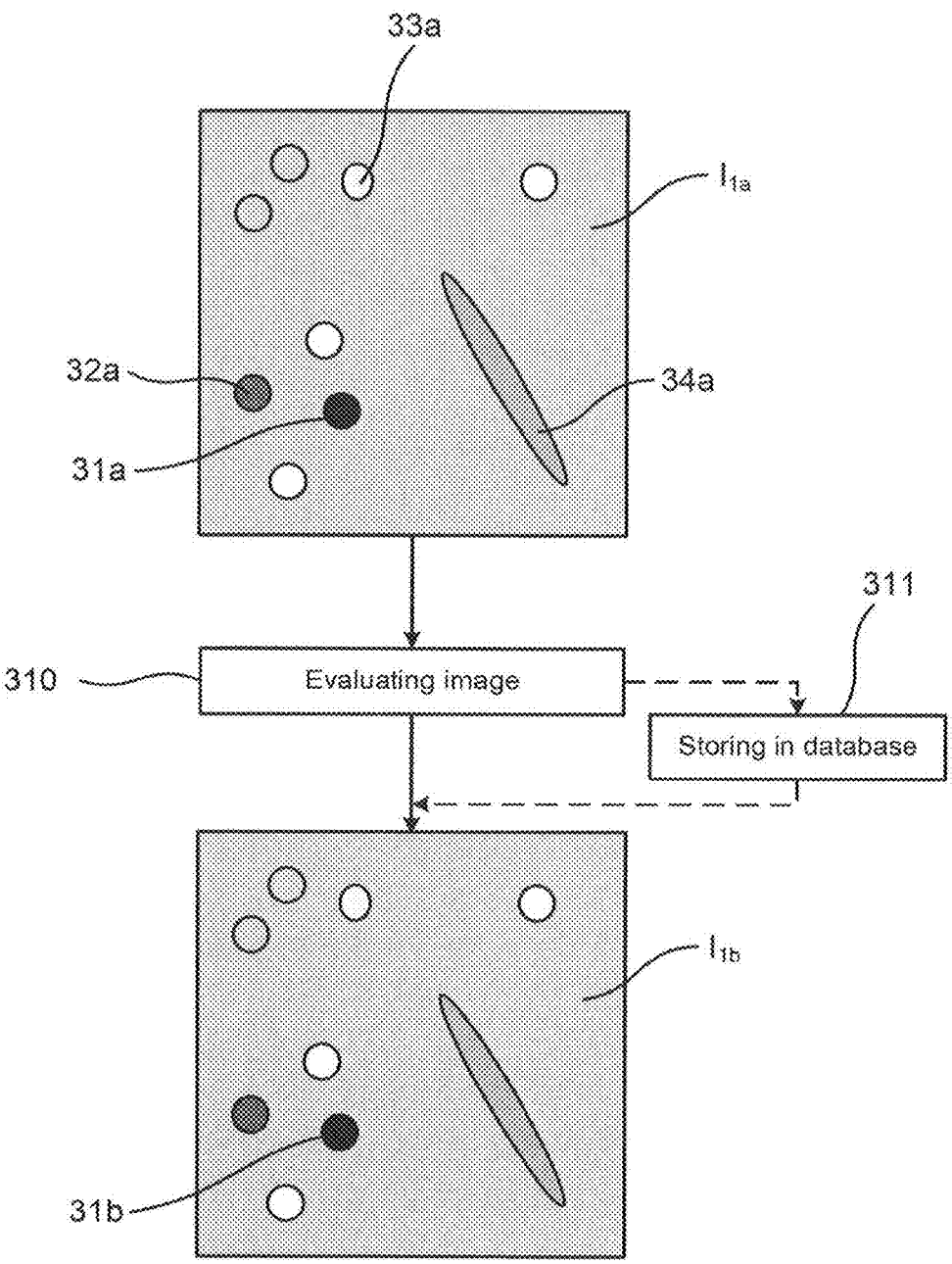
FIG. 3 illustrates an evaluation of a primary digital image.

FIG. 3 illustrates a primary digital image $I_{1a}$ depicting a tissue sample. The image originates from a cycle of the detection process disclosed above and as illustrated by FIG. 8. $I_{1a}$ comprises different elements and structures corresponding to elements and structures of the tissue section. For pedagogic reasons, the elements and structures of the tissue sample are represented as simplified geometrical shapes in FIG. 3. In reality, the image typically comprises thousands of elements and structures.

In this example, the detection process has been chosen such that the generation of detectable polymer leads to a colour shift in the area where the polymer is generated. The colour shift is such that the areas become darker. When affected by the detection process (step 815 in FIG. 8), areas where a generation of detectable polymer have been generated are referred to as undetermined marker areas. In FIG. 3, undetermined marker areas are indicated by 31a, 32a, 33a and 34a.

Since the areas are generated by detectable polymer, they may be identified by detecting the polymer.

In the present example, a greater generation of detectable polymer in an area yields a darker area. In an ideal detection process, generation of detectable polymer is only present in connection to elements which are aimed towards when choosing the particular molecular detection means. However, detectable polymer will frequently also be generated in other areas also due to cross-reactivity and non-specific binding of the detection antibody (or components used for molecular detection). The image may comprise further undetermined marker areas, which have not been affected by the detection process. It is desired to sort out areas most likely originating from "true" elements and structures, i.e. the elements and structures which are intended to be marked in a particular detection process cycle. Therefore, each image in the series of images is evaluated, as illustrated by step 310 in FIG. 3, according to predetermined selection criteria. The selection criteria are selected to suit the particular detection process.

The selection criteria may comprise a plurality of sub-criteria, such as:
  Colour threshold
  Colour interval
  Geometrical properties (shape and size parameters)
  Nature of the staining patterns within a marked area (e.g. texture parameters; granularity, coarsening, smooth even staining, dotted staining etc).
  Location (for example in relation to tissue structures that can e.g. be identified already in a non-stained section or after a background tissue staining).

To evaluate an image using these or similar criteria is known to the skilled person and could be done using software such as ImageJ provided by National Institute of Health (NIH), US; Image-Pro Plus by Media Cybernetica Inc, USA; Visiomorph by Visiopharm A/S Denmark; Definiens Tissue Studio by Definiens AG, Germany; Genie by Aperio Technologies, USA; MATLAB by Mathworks Inc, USA; Adobe Photoshop, etc.

By colour threshold is meant a threshold in a colour scale, such as a HLS (hue-lightness-saturation) colour scale, wherein a pixel with a colour value above or below the threshold of the particular colour scale fulfils the selection sub-criterion.

By colour interval is meant an interval within a colour scale, such as an R-value for a RGB colour scale image within a particular interval, such as 200-230. Areas with pixels having pixel values within the interval fulfill the selection sub-criterion.

Colour threshold and colour interval criteria are applicable with other colour scales as well, such as a HSB colour scale or HIS colour scales. Many other colour scales also exist as well known by the person skilled in the art.

By geometrical properties is meant parameters associated with the shape and/or size of the area. Examples are roundness, circularity, length, irregularity parameters etc. Shape value criteria can be used to define true elements/structures from untrue elements/structures by their shape. For example, nerves have an elongated shape whereby undetermined marker areas in an image, resulting from a detection process for nerves, which have other shapes than elongated can be excluded from being defined as image marker areas for the particular image.

As understood by the person skilled in the art, other suitable types of selection criteria may also be used in the present invention. By suitable is meant that the selection criteria are adapted to sort out the undetermined marker areas most likely originating from the elements and structures that are aimed towards in the particular corresponding detection process cycle.

In one embodiment, the selection criteria comprise a threshold for a visual property, such as a colour, texture, size, or roundness. By visual property is meant some kind of appearance characteristic of an marker area. Note that the property does not need to be visualized on e.g. an output unit in order to be a visual property.

The selection criteria may comprise one or more of the above mentioned criterion types. A combination of different types of criterion may also be comprised, such as a combination of a colour threshold criterion and a shape value criterion wherein both criteria must be fulfilled by an undetermined marker area in order to be defined as an image marker area.

In this example, the selection criteria comprise a visual property, more particular a colour threshold. Only areas with sufficient dark colour are defined as image marker areas and thus said to correlate to "true" elements and structures. Since this example comprises only grayscale colours, the colour threshold may be set to all pixels with a higher intensity a certain value on the grayscale. In a grayscale of 0-1 where 0 corresponds to black and 1 corresponds to white, a threshold value of 0.75 may be set. In other embodiments comprising images of another colour scale, e.g. a RGB colour scale, a threshold may be set in the corresponding way as understood by the person skilled in the art.

Different selection criteria yield different evaluation results and thus, different secondary images. In the present example of FIG. 3, the selection criteria comprise that pixels of an undetermined marker areas must be above a grayscale colour threshold. By the evaluation, a secondary digital image $I_{1b}$ with an image marker area 31b is obtained. The image marker area 31b is defined by evaluating the undetermined marker area 31a which fulfils the selection criteria. Other undetermined image marker areas 32a, 33a, 34a does not fulfill the selection criteria and hence, are not defined as image marker areas. In an additional step 311, the information of the evaluation, comprising for example geometrical spatial parameters (coordinates) or shape index of the evaluated marker areas, is stored in or in connection/association with the secondary image $I_{1b}$, such as in an associated database. Such a database may later on be updated with information regarding which undetermined marker areas that are defined as image marker areas. The information can be used to insert new image marker areas in the new image in the step 224.

The image $I_{1b}$ may be the exact same image as $I_{1a}$ or it may be copied and/or digitally edited, such as by inserting a visual mark by the image marker areas. However, the secondary digital image is not limited to being the same image as the primary digital image.

The difference between a secondary digital image and a primary digital image is that the secondary digital image has been evaluated in order to define image marker areas whereas a primary digital image is raw unedited and unevaluated data. Any edited or created digital image in the method is referred to as an secondary image since it is not any raw images obtained directly from digital imaging or scanning. Therefore, also new images created in, e.g., step 212 and 224 of the present invention is referred to as secondary digital images.

In one embodiment, a user may evaluate a primary digital image by use of an image software and defining image marker areas according to a predetermined selection criteria, such as a certain colour intensity, location surrounding and/or shape. Examples of image software useful for this kind of evaluation are Image-Pro Plus by Media Cybernetica Inc, USA; Visiomorph by Visiopharm A/S Denmark; Definiens Tissue Studio by Definiens AG, Germany; and Matlab by Mathworks Inc, USA.

The step 212 of creating a new image by inserting identifiable and categorized new markers corresponding to the defined image marker areas will now be described with reference to FIG. 4.

FIG. 4 discloses an image series of an embodiment of the present invention. Images $I_1$, $I_2$, $I_3$, $I_4$ form a series of N images, wherein N=4. The depicted object in each image is a tissue section (or a part of a tissue section). Each image comprises (the same part of) the same tissue section. The images has each been evaluated according to step 211 and step 222.

Each image comprises image marker areas: $I_1$ comprises an image marker area 411a; $I_2$ comprises image marker areas 411b and 421a; $I_3$ comprises image marker areas 411c, 421b, 431a, and 432a; and $I_4$ comprises image marker areas 411d, 421c, 431b, 432b, 441a, and 442a. Information relating to the image marker areas, such as location parameters, shape parameters, colour values, intensity values, etc., are preferably stored in or in connection/association with the image itself, such as in a database associated with the image. Such a database can be arranged in the memory 12. The parameters are for example stored according to the step 311 of FIG. 3 (described above).

As previously disclosed, the images in the image series comprise at least the same or typically an increasing amount of image marker areas. $I_4$ comprises the largest amount of image marker areas and $I_1$ comprises the least amount of image marker areas. $I_n$ comprises at least the same amount of image marker areas as $I_{n-1}$ for n=2, 3 or 4.

By comparing $I_4$, $I_3$ and/or information relating to them in the associated database, it is found that image marker areas 441a and 442a are present in $I_4$ but not in $I_3$. Thus, new image marker areas having the same shape and location as the image marker areas 441a and 442a are inserted in $I_{new}$ according to step 224. The new image marker areas are furthermore made identifiable by a unique feature, in particular a unique value of a unique feature.

Figure 5A:
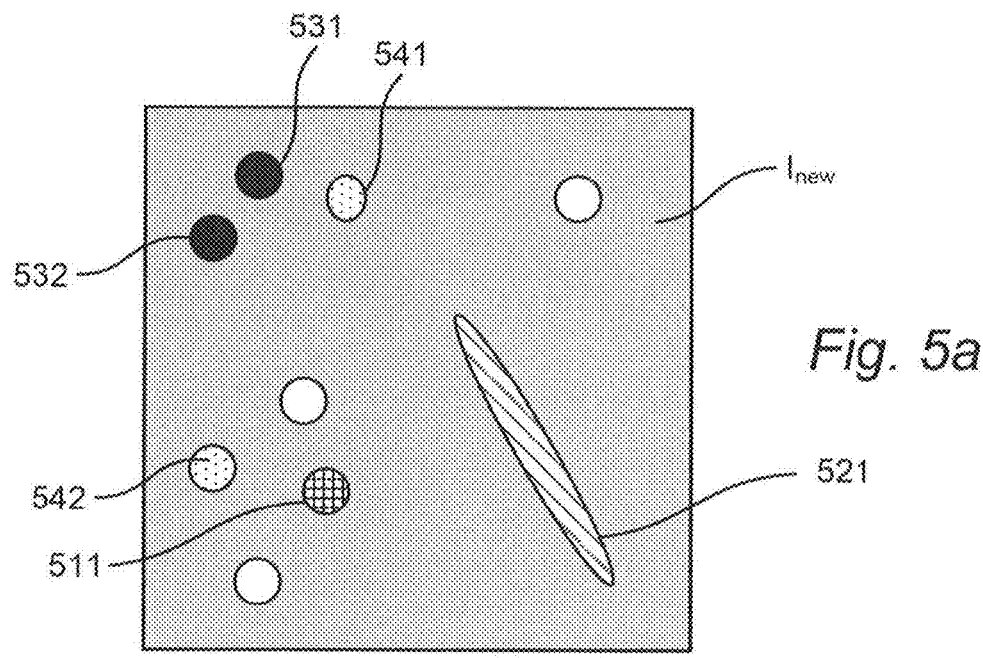
FIGS. 5a-b illustrate an images created by the method according to the present invention.
Figure 5B:
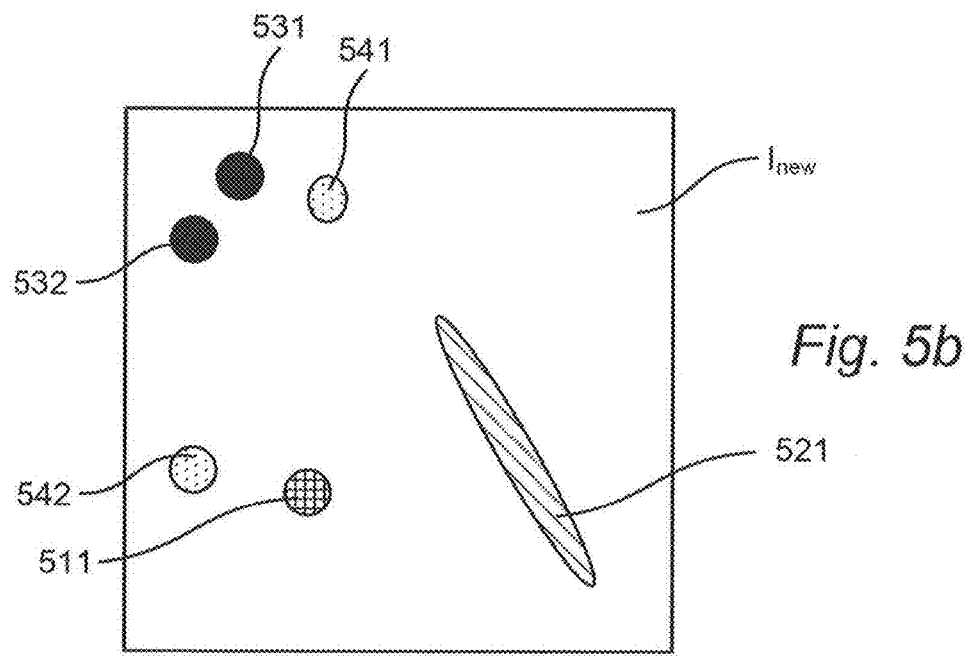

In FIGS. 5a and 5b, examples of new images are given. These may be obtained in the present example. The new image $I_{new}$ in FIG. 5a is provided by copying one of the images $I_1$-$I_4$, such as for example $I_1$. In FIG. 5b, the new image $I_{new}$ is provided by creating an empty image, i.e. without any information.

As disclosed above, new image marker areas having the same shape and location as the image marker areas 441a and 442a are inserted. In FIGS. 5a-5b, these are referred to as 541 and 542.

In FIGS. 5a-5b, the unique features are visual markers and comprise unique patterns for the inserted image marker areas of a specific group. The image marker areas 541 and 542 belong to a group areas being marked in the detection process cycle between the imaging of $I_3$ and the imaging of $I_4$. For the image marker areas 541 and 542, the visual marker of the unique feature is a dotted pattern.

In order to insert the image marker areas 541 and 542 with the same shape and location as image marker areas 441a and 442a, a database may comprise information referring to the image marker areas 441a and 442a. As disclosed above, such information may be stored in a database in the additional step 311 in FIG. 3. Furthermore, the method according to FIG. 2b may comprise an additional step of registering the shape and location of each image marker area identified according to predetermined selection criteria. By knowing the shape and location of the image marker areas 441a and 442b, the new image marker areas 541 and 542 can be inserted. As may be understood by the person skilled in the art, new image marker areas can be inserted in the new image by other procedures commonly known in the art.

By comparing $I_3$ with $I_2$, the image marker areas 431a and 432a are identified as present in $I_3$ but not in $I_2$. New image marker areas 531 and 532 with the same shape and location as the image marker areas 431a and 432a are inserted in $I_{new}$. In FIGS. 5a-5b, the visual marker of the unique feature of 531 and 532 is a filled pattern.

By comparing $I_2$ with $I_1$, the image marker area 421a is identified as present in $I_2$ but not in New image marker area 521 with the same shape and location as the image marker area 521a is inserted in $I_{new}$. In FIGS. 5a and 5b, the visual marker of the unique feature of 521 is a lined pattern.

Since $I_1$ is the result of the first cycle of detection process, $I_1$ does not need to be compared to any other image. In this example, image marker area 411a is identified as present in $I_1$ and thus originates from the detection process cycle generating $I_1$. A new marker area 511 is inserted in $I_{new}$ with the same shape and location as 411a. The image marker area 511 is furthermore made identifiable according to a unique feature. In FIGS. 5a and 5b, the visual marker of the unique feature of the image marker area 511 is a squared pattern.

Thereby a new image $I_{new}$ has been created comprising image marker areas categorized according to which detection cycle and consequently which cell marker and primary cell each image marker area represent. By the method of the present invention, multiple cells or tissue structures may be identified and categorized using an iteration of the same type of detection process. The used markers, such as detectable polymers or fluorochromes, for marking tissue elements or structures do not need to be unique in themselves. A single type of detectable polymer or a fluorochrome of a specific wavelength may be used in every cycle of the detection process, and generate marker areas having the same intensity, colour or light-emitting wavelength. This advantage is illustrated by the image $I_4$ in FIG. 4 and $I_{new}$ in for example FIG. 5a. With known techniques, the result of multiple detection processes generates the image $I_4$. Here, the marker areas are impossible to differentiate from each other, i.e. it is not possible to see which type of primary cell or tissue structure an image area in $I_4$ represents. However, by the novel concept of the present invention wherein multiple imaging is combined with the disclosed image analysis method, an image comprising image marker areas with categorization may be achieved in a simple and efficient way. Many problems with known techniques, such as the limitation of detecting multiple markers within the same section, may thus be overcome.

Figure 6A:
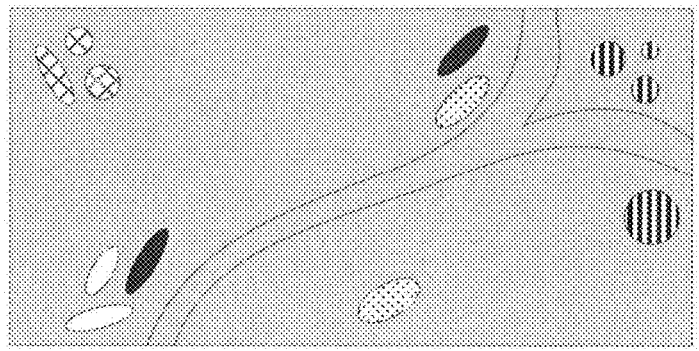
FIGS. 6a-c illustrate different visual unique features of image marker areas in images created by the method according to the present invention.
Figure 6B:
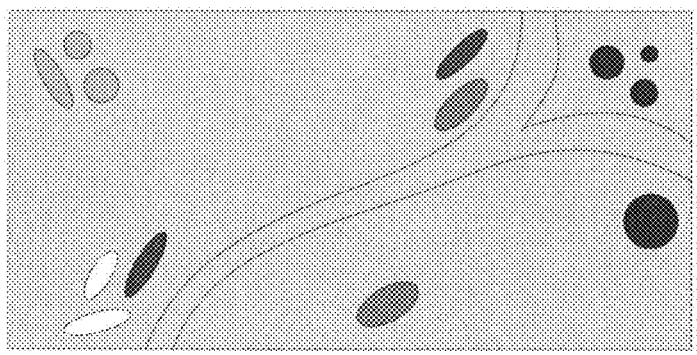

FIGS. 6a-6b illustrate examples of unique visual features for the categorized image marker areas in the image $I_{new}$ according to the present invention. The images depict a tissue sample with elements and structures. The images have been provided through the method of the present invention.

In FIG. 6a, the unique feature is different patterns.

In FIG. 6b, the unique feature is the colour gray and the unique values are intensities of the gray colour and in particular different grayscale intensities. A new image could comprise a plurality of features, such as different colours, and said such colours could be further subdivided into unique values which values could be different intensities of said different colours.

Figure 6C:
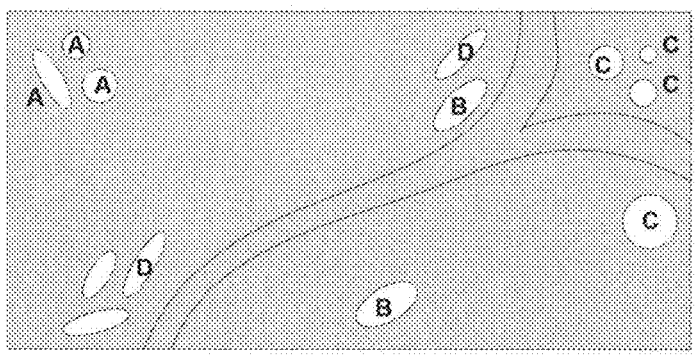

In FIG. 6c, the unique feature is different symbols. In this embodiment, the symbols are characters, but they could equal as well be digits, geometrical symbols, etc. or a combination thereof. The symbols are arranged in the digital image $I_{new}$ nearby the image marker area it represents, such that it is clear which image marker it is associated with.

As mentioned earlier, it should be noted that the unique feature not necessarily need to be a visual feature arranged in the new image. It could instead of, or in combination with, a visual marker be digital information, such as a unique digital value, where the image marker areas of a group are associated with each other. Such information may be stored in a database, and preferably in the above mentioned database comprising information pertaining to location, shape, and other staining characteristics of image marker areas.

Figure 7:
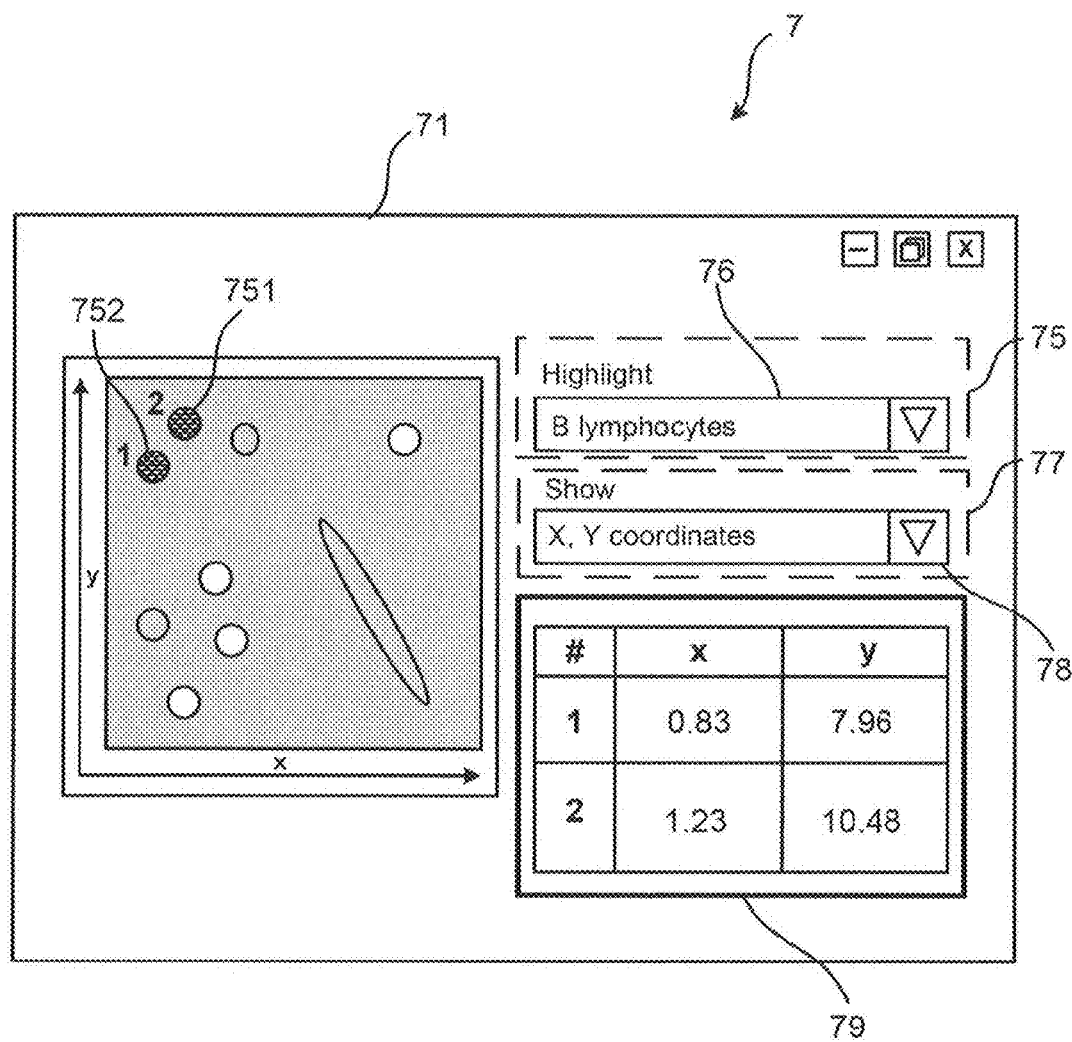
FIG. 7 illustrates graphical interface according to an embodiment of the present invention.

FIG. 7 illustrates an embodiment of the present invention where a graphical interface, generally given by 7, is used to provide a user with information pertaining to the method of the present invention. A computer program providing the graphical interface 7 may be stored in the memory 12 and executed by the processor 11. The computer program may alternatively be stored on any suitable storage unit, such as a USB stick or a CD-ROM. The computer program may furthermore execute the method of differentiating marker areas in a series of images according to the present invention.

The graphical interface 7 comprises a graphical window 71 which is provided to a user through an output unit 14, such as a computer screen, in connection to the apparatus 10. The user can provide the computer program with input, such as a selection, by an input unit 15, such as a computer mouse or keyboard, in connection to the apparatus 10.

The graphical window 71 comprises an image 72 corresponding to a new image $I_{new}$ provided by the method according to the present invention. In this embodiment, the image 72 depicts the same tissue section as in FIGS. 4-5.

The graphical window 71 further comprises at least one box 75 for adapting how to view the image 72. The box 75 may comprise a choice box 76 for providing a choice between different alternatives. In this embodiment, the box 75 provides a choice of which group of primary cell populations to highlight in the image 72. By choosing the alternative "B lymphocytes" in the choice box 76, the image marker areas 751 and 752 associated with the B lymphocyte primary cells are highlighted. The association between an image marker area and a primary cell may be stored in a database, wherein the information pertaining to the association may be obtained by the computer program from the database. The database may be achieved by the method according to the present invention as disclosed above, in particular by the step 311. The alternatives provided by the box 75 is not limited to comprise only one type of cell types, but could equally as well comprise a group of a plurality of cell types.

The graphical window 71 may comprise further multiple choice boxes or other suitable adaption means such as check boxes, multiple choice windows, etc.

The graphical window 71 further comprises a box 77 associated with a information box 79. The provided information in the information box is associated with image marker areas of image 72. The information can be obtained by a database comprising information pertaining to image marker areas of the image 72. The choice box 77 comprises a choice box 78. The user can choose between different information types in order to show specific such information about image marker areas in information box 79. In this illustrated example, the user has chosen to show coordinates by selecting the alternative "X, Y coordinates" in the choice box 78. Information pertaining to the x and y coordinates of the highlighted image marker areas 751 and 752, chosen by choice box 76, is provided by the information box 79.

Of course, the graphical interface 7 may take many different forms and comprise many different functions. Thus, the type of information pertaining to image marker areas which may be provided to the user by the graphical interface 7 is not limited by this example. By the claimed method, a user may be provided with information such as:

the area, expressed in e.g. $\mu m^2$, for any maker area.

shape values for an image marker area, e.g. perimeter and roundness intensity values, e.g. mean intensity of pixels in an image marker area distances within the image, e.g. distances between two image marker areas spatial correlations between image marker areas, or groups of marker areas; For example, through use of statistics algorithms in the software, a user may get information about the spatial relationship between e.g. marker areas corresponding to B-lymphocytes and those marker areas in the same tissue area that correspond to the cell population of e.g. T-lymphocytes.

It should be noted that when applying the present invention to serially cut tissue sections (e.g. 30 consecutive sections, each with a fixed thickness of e.g. 4 $\mu m^2$) a similar graphical interface such as revealed in FIG. 7 may also display the three dimensional distribution of image marker areas in an 3D image. Similarly, a user may then obtain 3D information about image marker areas, such as their x, y, and z coordinates. Through use of commonly known algorithms for 3D rendering a user may obtain calculations (or graphical displays) about the volume of a marked cell or tissue structure.

The computer program and graphical interface 7 should be seen as means for providing a user with any information which may be extracted from the images of the method of the present invention. How to extract and store such information in, e.g., a database is general knowledge for a person skilled in the art. How to form a computer program in order to accomplish the features described in connection to the above may also be accomplished by a person with a general knowledge in the art. It should be noted that the computer program is not limited to the features described above, and could for example comprise further well-known features such as editing and reviewing digital images. The graphical interface 7 could furthermore also comprise features for performing the evaluation of primary digital images.

In summary, the present application discloses a method for differentiating areas in a series of digital images, the method comprising the steps of: providing a series of images comprising undetermined marker areas; evaluating every image $I_n$ for $1 \leq n \leq N$ according to predetermined selection criteria and defining image marker areas as undetermined marker areas fulfilling the predetermined selection criteria; providing a new image $I_{new}$; and inserting new image marker areas in the new image $I_{new}$, said new image marker areas having the same shape and location as image marker areas present in image $I_n$ but not in image $I_{n-1}$, and said new image marker areas being identifiable in $I_{new}$ by a unique feature.

Further, the application discloses a method for visualizing cell populations in tissue sections of a histological sample.

Further, the application discloses a method for visualizing three-dimensional distribution of multiple cell populations in a histological sample.

EXAMPLES

The present invention will now be further disclosed with reference to the enclosed examples.

Example 1

Tissue Handling, Sample Preparation, and Generation of Sections

The following human tissues were included:

Human distal colon: surgical resection due to chronic inflammation and suspected non-specific colitis.

Human lung tissue from patients with Chronic Obstructive Pulmonary Disease, COPD and Cystic Fibrosis: lung resection due to suspected lung cancer, the analyzed tissue was not affected by cancer and obtained as far away from the tumour as possible.

Human lymph nodes: Large draining lymph nodes collected in association with lung transplantation due to severe COPD or cystic fibrosis.

Human tonsils: collected as part of routine tonsillectomy due to repeated episodes of tonsillitis.

Samples (i.e. blocks of tissue) from all tissue types were immersed subjected to routine fixation by immersion into routine fixative (4% buffered formaldehyde, pH 7.6). After fixation overnight, the samples were dehydrated in a series of solutions with increasing concentration of alcohol (EtOH) and final immersion into xylene. The dehydration was carried out in an automated dehydration machine (Shandon Hypercenter XP Tissue Processor, Shandon/ThermoFisher Scientific, Waltham, Mass., USA). The dehydrated specimens were thereafter embedded in paraffin at 60° C. using a paraffin-embedding machine. Paraffin sections (4 $\mu m$) were generated with a routine paraffin-cutting microtome (Microm HM360 paraffin microtome, Microm, Germany) and mounted on standard microscope glass slides. Sections were then stored at 4° C. until use.

Example 2

Multiple Immunohistochemical Staining and Generation of Serial Digital Images

Immunohistochemical staining was performed using an automated immunohistochemistry robot (Autostainer CL-classic; Dako Cytomation, Glostrup, Denmark) with the DAKO REAL EnVision detection system), a sensitive standard method intended for detection of primary mouse or rabbit antibodies (IHC kit Code K5007, Dako Cytomation, Denmark; for details see www.dako.com). The primary antibodies used to detect the cell-specific antigens (earlier referred to as "cell markers") are listed in Table 2 and applied onto the sections at the dilution recommended by the commercial producers for immunohistochemical staining of human tissues prepared for routine pathological examination (i.e. sections from formalin-fixed and paraffin-embedded samples). Examples of series of markers that were used in the evaluation of ESMS are listed in Table 3.

TABLE 2

Examples of Antibodies Used for Experimental Validation of the ESMS Technique

| Marker | Primary Cell Type | Provider |
|---|---|---|
| CD20 | B-lymphocytes | Dako |
| CD3 | T-lymphocytes | Dako |
| CD8 | CD8+ T lymphocytes | Dako |
| ECP (EG2) | Eosinophils | Pharmacia |
| Tryptase | MCt Mast Cells | Chemicon |
| Chymase | MCtc Mast Cells | Chemikon |
| CD68 | Macrophages/monocytes (also basophils, large lymphocytes) | Dako |
| MPO | Neutrophils | Dako |
| CD163 | Most tissue macrophages | Novocastra |
| CD123 | Plasmacytoid DC (also monocytes, basophils, neutrophils, eosinophils) | BD-Pharmingen |
| CD1a | Intraepithelial dendritic cells | Novocastra |
| CD11c | Myloid Dendritic Cells (but also e.g. macrophages) | Novocastra |
| BDCA-3 | Subpopulation of Myloid Dendritic cells | Novus |
| CD21 | Follicular Dendritic Cells | Dako |
| Viementin | Foremost Fibroblasts | Novocastra |
| Cytokeratin | Epithelial cells | Novocastra |
| Lyve-1 | Lymphatic vessels | Dako |
| Caveolin-1 | Endothelial Cells (blood vessels) | Novocastra |
| Neuron-Specific Enolase (NSE) | Nerves (and epithelial neuroendocrine cells) | Novocastra |
| Alpha- Smooth muscle actin | Smooth muscle tissue | Sigma-Aldrich |

Before the actual immunohistochemistry step, the paraffin sections were deparaffinized and subjected to heat-induced antigen retrieval. This procedure was carried out using a commercial and programmable antigen-retrieval machine (PT Link from Dako Cytomation, Denmark) with a peak temperature at 95° C. and the Envision FLEX Target Retrieval Solution, pH 6.1 (Dako Cytomation).

After antigen retrieval, the slides were placed in the Autostainer Robot The programmed immunohistochemical protocol was as follows:

1) Rinse step with Envision FLEX wash buffer (pH 7.6) for 5 min.
2) Block of endogenous peroxidase in 0.3% $H_2O_2$ in $dH_2O$ (10 min).
3) Incubation with appropriately diluted primary antibodies (see table 2) for 60 min. The antibodies were diluted in a PBS buffer supplemented with 01% tween detergent.
4) Rinse step with Envision FLEX wash buffer (pH 7.6) for 5 min.
5) Incubation for 30 mins with secondary reagent (anti-mouse and anti-rabbit antibodies linked to a dextran polymer with attached detection enzyme, HR Peroxidase (HRP).
6) Repeated rinse steps with Envision FLEX wash buffer (pH7.6) for 5 mins.
7) Incubation with HRP enzyme substrate (diaminobenzidine, DAB) solution for 10 min.
8) Repeated rinse steps with Envision FLEX wash buffer (pH7.6) for 5 min.
9) The developed sections were gently mounted with standard cover slips using PBS buffer supplemented with 0.1% tween as mounting medium.
10) Next information of the staining pattern in each section was digitalized. The brown insoluble precipitation formed by the HRP enzyme at the site of immunoreactivity was captured throughout the entire section using a commercial whole slide scanner robot (Aperio Scanscope CS, Aperio Technology, USA). The digitalization was performed using a ×20 microscope lens and the size of the generated ultra-high-resolution image for each section was typically 2-5 GB in size (and originally in a SVS image file format; parts of the large SVS image were also exported as TIFF images using the export features provided by the ImageScope software provided by Aperio, see below).
11) Alternatively, or as a complement to the whole-slide digitalization, selected regions from the sections were also captured at higher magnification (×400 or 600; TIFF or JPEG images) using a bright field microscope (Nikon 80i Research Microscope, Nikon, Japan) equipped with a colour digital camera (Olympus DP-50, Olympus, Japan) and an image capture software (Viewfinder Lite, v1.0, 2000, Pixera Co).
12) After digitalization, the cover slips were gently removed and the slides were rinsed in buffer before entering a new immunohistochemistry cycle (starting at step 2 in the protocol). In some cases, before the sections were entered into the next staining cycle they were immersed in a blocking solution that make the previous primary antibodies unrecognizable to the secondary detection antibodies in the subsequent staining cycle. The disruption of the antigen recognition site was carried out by chemical modification. Such chemical modification was done in two different ways. The antigen recognition site was either destructed by protein denaturation using the denaturizing blocking solution DNS001H from BioCARE, Concord, Calif., US. Alternatively, the antibodies could be enzymatically cleaved.
13) Next, the section entered into a new staining cycle starting with step 2 ($H_2O_2$ block in the protocol above).
14) After n numbers of cycles and development of the final marker immunoreactivity the sections are rinsed in ddH20, counter stained with haematoxylin (Htx, Merck, Darmstadt, Germany), dehydrated through a series of alcohol solutions and xylene, and finally mounted with Pertex mounting media (HistoLab, Gothenburg, Sweden) before being digitalized as described above.

TABLE 3

Examples of Marker Series Used in the Validation of the ESMS Technique

|  | Cycle-1 | Cycle-2 | Cycle-3 | Cycle-4 | Cycle-5 | Cycle-6 | Cycle-7 | Cycle-8 |
|---|---|---|---|---|---|---|---|---|
| Polyp |  |  |  |  |  |  |  |  |
| Section 1 | CD20 | CD8 | ECP | Trypt | MPO | CD68 | Cytok | Viement |
| Section 2 | CD20 | CD8 | ECP | Trypt | NSE | Lyve-1 | Cytok |  |
| Section 3 | CD8 | EG2 | MPO | SMA | NSE | Lyve-1 | Cytok |  |
| Colon |  |  |  |  |  |  |  |  |
| Section 1 | CD20 | CD8 | ECP | Trypt | CD68 | CD11c | Cytok | Viement |
| Section 2 | CD20 | CD8 | ECP | Trypt | NSE | SMA | Cytok | CD68 |
| Section 3 | CD20 | CD8 | CD3 | CD68 | ECP | Chym | Trypt | MPO |
| Lymph node |  |  |  |  |  |  |  |  |
| Section 1 | CD21 | CD68 | CD11c | BDCA-3 | CD20 | CD8 | SMA |  |
| Section 2 | CD20 | CD3 | CD21 | CD11c | Chym | Trypt |  |  |
| Section 3 | CD21 | CD3 | CD68 | CD20 | Chym | Trypt |  |  |
| Lunga |  |  |  |  |  |  |  |  |
| Section 1 | CD20 | CD8 | CD3 | CD68 | ECP | Chym | Trypt | MPO |
| Section 2 | CD20 | CD8 | CD3 | CD68 | CD11c | ECP | MPO | Trypt |
| Section 5 | CD20 | CD8 | Trypt | NSE | Cytok | SMA | Lyve-1 | CD68 |
| Section 6 | NSE | CD8 | Trypt | Lyve-1 | Cytok | SMA | CD68 | Viement |
| Section 7 | NSE | CD1a | CD68 | BDCA-3 | CD11c | SMA | Cytok |  |

SMA = alpha smooth muscle actin,
Chym = Chymase,
Trypt = Tryptase,
Cytok = cytokeratin,
NSE = Neuron Specific Enolase Example 3

Computerized Image Analysis and Decoding of Marker-Specific Staining Patterns

Digitalized sections from Aperio's slide scanner, corresponding to a series of primary images according to the disclosed invention, were inspected manually using a viewing software (Aperio ImageScope, version 10.0.35.1798, Aperio Technologies Inc). In the initial evaluation regions of interest in each section were selected for further detailed analysis. Using the extract and export image function in the ImageScope software, raw images, i.e. primary digital images, were exported as TIFF or JPEG files; one image for each staining cycle. Together, the images formed one series of images per region of interest.

For some images the distribution pattern of the brown DAB precipitation was outlined already before the image export by the colour segmentation features ("positive pixel" algorithm) included in the ImageScope software after selecting RGB and Hue values characteristic of the brown DAB precipitation.

In case the brown immune staining, i.e. image marker areas, had not already been outlined in ImageScope, this was performed using readily available software with colour recognition functions (e.g. ImageJ, version 1.44o, National Institute of Health (NIH), USA or Adobe Photoshop® CS4 Extended, version 11.0.2, Adobe Systems Incorporated, USA). Through visual feedback of detected spots, a person with knowledge about the typical staining pattern and staining appearance of each cell type fine-tuned the threshold values until optimal detection was produced.

Next, the series of images, with the accumulated undetermined image marker areas produced after each molecular detection cycle, were evaluated. The image marker areas were then digitally cut out and given a pseudo colour unique for the corresponding cycle of detection process. Using the last image, i.e. image N in the series of N images, as a template the colour-coded accumulated staining dots, i.e. coloured image marker areas, were copy-pasted onto the template in a backward order (if needed this procedure was preceded by an alignment step that, by using the tissue contour as reference points, corrected for occasional minor differences in physical orientation among images within the same series).

For example, in the case of a image series with seven images, i.e. resulting from seven detection process cycles, a copy of the last image (the seventh), with all accumulated staining was used as the new image template. It is in some embodiments advantageous to copy the last since it has the best morphology due to that the slide with the tissue section was finally and optimally mounted in non-aqueous mounting medium before generating the last primary digital image. The image marker areas in the sixth image were copy-pasted into the new image. Image marker areas already present in the new image were thus masked, i.e. marker areas that were not generated in the seventh detection round were masked. Similarly, the image marker areas in the fifth image masked all image marker areas that were not generated in the sixth detection process round.

The generated composite new image eventually displayed seven distinct colours: one for each group of image marker areas originating from different staining cycles, i.e. detection process cycles.

Information could be extracted from the new image by automatically select a marker colour (using e.g. the ImageJ software or MATLAB®) and then use the "analyse particle algorithm", or similar operation, to generate detailed information about each stained spot (perimeter, area, shape index, x, y coordinates for the centroid of the spot etc.). This function may also be included in the disclosed graphical user interface (illustrated by FIG. 7).

Another approach for generation of composite images by evaluating the image series was to use the colour segmentation tools and analyze particle tools provided by Image J (v 1.44) and freely available plug-ins for Image J. Briefly, each image in the series was subjected to the following procedure:

1) the brown DAB-stained spots, i.e. the image marker areas, were segmented out by colour-based segmentation by evaluating the images with selection criteria comprising appropriate HSB (Hue, Saturation, Brightness) threshold values;

2) the images were transformed to a binary black/white image (i.e. binarised)

3) the transformed images from step 2) were evaluated using the analyze particle tool of Image J (version 1.44) with appropriate size restrictions and a data list, i.e. a database, of all image marker areas, i.e. all stained marker areas, was produced and stored. The data list contained the x,y coordinates, area, perimeter, circularity, roundness, mean staining intensity, etc. for all individual image marker areas. The program automatically produced an marked up image where the marker areas are outlined together with the marker area number that corresponds to the same spot in the data list.

Next, by comparing the numeric values of the marker area distribution (i.e. the x,y coordinates) it was possible to calculate which image areas that were present in for example image n but not in n−1. This approach was performed on all pair of consecutive images thus producing information about which image marker that appeared after each new molecular detection cycle. Finally, using this information, together with the data list of all accumulated marker areas from the last image, it was possible to create a new composite image. After activating the Region Of Interest (ROI)-manager each marker areas belonging to a specific molecular detection cycle was given a specific colour in the corresponding marked up image.

In order to illustrate an advantage of the information that can be extracted, let's consider the scenario of an inflamed tissue and staining for multiple populations of tissue-infiltrating immune cells (leukocytes). In a conventional routine section there are typically tens of thousands cells of each population. Extracting x, y coordinates for individual cells within multiple leukocyte populations makes it possible to perform a new type of powerful analysis of cell patterns. For example, the relative new and emerging field of spatial analysis (spatial statistics) and cluster analysis can be performed to obtain information about potentially disease-specific cell constellations (infiltration patterns), which cells that attract each other, or are attracted to certain micro-localizations in the tissue, or certain combinations of cells etc.

The invention claimed is:

1. A method of differentiating areas in a series of N primary digital images of a tissue section wherein N is an integer >1, thereby creating a new image, said method comprising:
    a) providing a series of N primary digital images comprising undetermined marker areas, wherein an image $I_{n+1}$ comprises at least the same amount of undetermined marker areas as a primary digital image $I_n$ for $2<n<N$, wherein n is an integer;
    b) evaluating every primary digital image $I_n$ for $1<n<N$ according to predetermined selection criteria and defining image marker areas as undetermined marker areas fulfilling the predetermined selection criteria, thereby obtaining a series of N secondary digital images, and storing information about any such image marker area in or in connection/association with a corresponding secondary digital image in the obtained series of secondary digital images;
    c) providing a new image $I_{new}$;
    d) for every n for $2<n<N$ of the series of secondary digital images obtained in operation b), inserting new image marker areas in the new image $I_{new}$, said new image marker areas having the same shape and location as image marker areas present in image $I_n$ but not in image $I_{n-1}$, said new image marker areas being identifiable in $I_{new}$ by a unique feature;
    e) inserting new image marker areas in the new image $I_{new}$, said new image marker areas having the same shape and location as image marker areas present in image $I_1$, and said image marker areas being identifiable in $I_{new}$, by a unique feature.

2. A method according to claim 1, wherein the providing a new image $I_{new}$ comprises providing an image of the tissue section.

3. A method according to claim 2, wherein the new image $I_{new}$ is a copy of one of the images in said series of primary digital images.

4. A method according to claim 1, wherein said unique feature in operations d) and e) is a feature that has a unique value for each n, $1<n<N$.

5. A method according to claim 4, wherein said unique feature is a general colour and said unique value of said unique feature is a specific colour associated with a particular cell marker.

6. A method according to claim 1, wherein the predetermined selection criteria comprise a threshold for a visual property of an undetermined marker area.

7. A method for visualizing cell populations within a histological tissue section, said method comprising:
    I) providing a tissue section that has been rendered ready for molecular staining;
    II) providing a series of K particular molecular detection means for specifically binding to and detecting members of a predetermined series of K cell markers that may be present in the tissue section of operation I), said series of particular molecular detection means being capable of generating formation of an initiable and detectable response, K being an integer >2;
    III) for each particular molecular detection means k=1, 2, ..., K of operation II) carrying out the following procedure:
        1) contacting said tissue section of operation I) with a corresponding one of the series of particular molecular detection means resulting in specific binding to a particular member of said predetermined series of cell markers;
        2) washing said tissue section in order to remove molecular detection means that has not been bound to any cell marker;
        3) initiating response from molecular detection means that may have bound to cell markers of the tissue section thereby enabling detection of said molecular detection means; and
        4) when said molecular detection means can be detected, scanning/imaging the tissue section in order generate a primary digital image $I_k$ that may contain one or more undetermined marker areas associated with generation of a detectable polymer;
    whereby a series of K primary digital images $I_k$ for k=1, ..., K containing an increasing amount of undetermined Marker areas is obtained;
    IV) carrying out the method of claim 1 on the series of K primary digital images $I_k$ for k=1, ..., K obtained in operation III), thereby generating an image $I_{new}$ visualizing said cell structures.

8. A method according to claim 7, wherein said molecular detection means are a set of antibodies, wherein each antibody binds to a specific cell marker and wherein an enzyme has been conjugated to each antibody, said enzyme being capable of generating formation of a detectable polymer in presence of one or more suitable substrates, wherein operations 1) and 2) of operation III) are carried out in such a way that:
i) the tissue section of operation I) is contacted with an antibody specifically binding to a particular member of said predetermined series of cell markers; said antibody being conjugated to an enzyme, said enzyme being capable of generating formation of a detectable polymer in presence of one or more suitable substrates;
ii) after operation i) above, the tissue section is washed in order to remove unbound antibodies; and wherein operation 3) of operation III) is carried out in such a way that:
iii) after operation 2) the tissue section is exposed to one or more suitable substrates for said enzyme, leading to formation of detectable polymers in case said particular member of said predetermined series of cell markers is present in said tissue section.

9. A method according to claim 7, wherein said molecular detection means are a set of molecular complexes, where each complex comprises a first antibody, binding to a specific cell marker, a second antibody or an antibody fragment specifically bound to said first antibody, and an enzyme conjugated to said second antibody, said enzyme being capable of generating formation of a detectable polymer in presence of one or more suitable substrates, wherein operations 1) and 2) of operation III) is carried out in such a way that:
i) the tissue section of operation I) is contacted with a first antibody specifically binding to a particular member of said predetermined series of cell markers;
ii) after operation i) above, the tissue section is washed in order to remove unbound antibodies;
iii) after operation ii) above, the tissue section is contacted with a second antibody specifically binding to said first antibody, said second antibody being conjugated to an enzyme, said enzyme being capable of generating formation of a detectable polymer in presence of one or more suitable substrates; and
iv) after operation iii) above, the tissue section is washed in order to remove unbound antibodies; and wherein operation 3) of operation III) is carried out in such a way that:
v) after operation 2) the tissue section is exposed to one or more suitable substrates for said enzyme, leading to formation of detectable polymers in case said particular member of said predetermined series of cell markers is present in said tissue section.

10. A method according to claim 8, wherein said enzyme is chosen from the group of alkaline phosphatase and peroxidase.

11. A method according to claim 10, wherein said substrate is selected from the group of 3,3'-diaminobenzidine, Ferangi Blue, Vulcan Fast Red, aminoethyl carbazole (AEC), and Vina green.

12. A method according to claim 7, wherein said molecular detection means are a set of molecular conjugates comprising a recognizing part bound to a detecting part, wherein said recognizing part is capable of specifically binding to a particular member of said predetermined series of cell markers, said recognizing part being selected from the group of an antibody, and a nucleic acid molecule, said detecting part being a fluorochrome, said fluorochrome being capable of emitting radiation of a particular wave length after exposure to initiating radiation different from said emitted radiation wherein operation 3) of operation III) is carried out in such a way that the tissue section and any molecular detection means that have been bound thereto are exposed to initiating radiation leading to emission of radiation of a particular wave length in case said particular member of said predetermined series of cell markers is present in said tissue section; and wherein operation 4) of operation III) is carried out when said radiation of a particular wave length is emitted.

13. A method according to claim 8, wherein a substrate generating at least partially soluble polymers is used as a substrate for producing a detectable polymer, the method further comprising:
V) washing said tissue section in order to remove said detectable polymer; and
VI) repeating operations II-IV with a new series of molecular detection means.

14. A method for visualizing the three-dimensional distribution of multiple cell populations and cell structures within the same three-dimensional space in a histological sample, comprising:
A) providing a tissue sample, and cutting said sample in a plurality of originally superposed tissue sections;
B) carrying out the method according to claim 7 for all tissue sections obtained in operation A); and
C) superposing the images obtained in operation, thereby obtaining a three-dimensional visualization of the three-dimensional distribution of multiple cell populations and cell structures within the same three-dimensional space in a histological sample.

15. A method according to claim 8, wherein the set of antibodies includes monoclonal antibodies or antibody fragments.

16. A method according to claim 9, wherein the first antibody and the second antibody or antibody fragment are monoclonal antibodies.

17. A method according to claim 10, wherein said peroxidase is horseradish peroxidase.

18. A method according to claim 12, wherein the antibody is a polyclonal antibody, a monoclonal antibody or fragments thereof.

19. A method according to claim 12, wherein the nucleic acid molecule is an RNA molecule or a DNA molecule.

20. A method according to claim 13, wherein the detectable polymers are Vina green or aminoethyl carbazole (AEC).

* * * * *